US007655002B2

(12) United States Patent
Myers

(10) Patent No.: US 7,655,002 B2
(45) Date of Patent: Feb. 2, 2010

(54) LENTICULAR REFRACTIVE SURGERY OF PRESBYOPIA, OTHER REFRACTIVE ERRORS, AND CATARACT RETARDATION

(75) Inventor: Raymond I. Myers, Collinsville, IL (US)

(73) Assignee: Second Sight Laser Technologies, Inc., Collinsville, IL (US)

( * ) Notice: Subject to any disclaimer, the term of this patent is extended or adjusted under 35 U.S.C. 154(b) by 679 days.

(21) Appl. No.: 10/750,789

(22) Filed: Jan. 2, 2004

(65) Prior Publication Data

US 2004/0199149 A1    Oct. 7, 2004

Related U.S. Application Data

(63) Continuation-in-part of application No. 09/897,585, filed on Jun. 29, 2001, now abandoned, which is a continuation of application No. 09/312,518, filed on May 14, 1999, now abandoned, which is a continuation of application No. 08/821,903, filed on Mar. 21, 1997, now abandoned.

(60) Provisional application No. 60/036,904, filed on Feb. 5, 1997, provisional application No. 60/013,791, filed on Mar. 21, 1996.

(51) Int. Cl.
*A61F 9/008* (2006.01)
(52) U.S. Cl. ............................... 606/5; 606/10
(58) Field of Classification Search .......... 606/3–6, 606/10–13
See application file for complete search history.

(56) References Cited

U.S. PATENT DOCUMENTS

| 3,971,382 A | 7/1976 | Krasnov |
| 3,982,541 A | 9/1976 | L'Esperance |
| 4,024,852 A | 5/1977 | L'Esperance et al. |
| 4,263,893 A | 4/1981 | Pavlak et al. |
| 4,381,007 A | 4/1983 | Doss |
| 4,394,144 A | 7/1983 | Aoki |
| 4,461,294 A | 7/1984 | Baron |
| 4,477,159 A | 10/1984 | Mizuno et al. |
| 4,502,816 A | 3/1985 | Creter et al. |

(Continued)

FOREIGN PATENT DOCUMENTS

WO    2005070358 A1    1/2005

OTHER PUBLICATIONS

Breitenfeld, P., et al., "Finite Element Method-Simulation of the Human Lens during Accomodation," Therapeutic Laser Applications and Laser-Tissue Interactions II, Proceedings of the SPIE, 2005, pp. 1-9, vol. 5863.

(Continued)

*Primary Examiner*—David Shay
(74) *Attorney, Agent, or Firm*—Brinks Hofer Gilson & Lione

(57) ABSTRACT

Methods for the creation of microspheres treat the clear, intact crystalline lens of the eye with energy pulses, such as from lasers, for the purpose of correcting presbyopia, other refractive errors, and for the retardation and prevention of cataracts. Microsphere formation in non-contiguous patterns or in contiguous volumes works to change the flexure, mass, or shape of the crystalline lens in order to maintain or reestablish the focus of light passing through the ocular lens onto the macular area, and to maintain or reestablish fluid transport within the ocular lens.

10 Claims, 8 Drawing Sheets

U.S. PATENT DOCUMENTS

| | | |
|---|---|---|
| 4,517,980 A | 5/1985 | Tagnon |
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance, Jr. |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,747,612 A | 5/1988 | Biurnaruber et al. |
| 4,758,081 A | 7/1988 | Barnes |
| 4,765,336 A | 8/1988 | Blaha et al. |
| 4,770,162 A | 9/1988 | L'Esperance |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi et al. |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiuama |
| 4,901,718 A | 2/1990 | Bille et al. |
| 4,903,695 A | 2/1990 | Warner et al. |
| 4,905,711 A | 3/1990 | Bennett et al. |
| 4,907,586 A * | 3/1990 | Bille et al. .................... 606/5 |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,098,426 A | 3/1992 | Sklar et al. |
| 5,102,409 A | 4/1992 | Balaorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance et al. |
| 5,152,759 A | 10/1992 | Parel et al. |
| 5,163,934 A | 11/1992 | Munnerlun |
| 5,171,242 A | 12/1992 | Dewey et al. |
| 5,174,021 A | 12/1992 | L'Esperance et al. |
| 5,178,635 A | 1/1993 | Gwon et al. |
| 5,188,631 A | 2/1993 | L'Esperance, Jr. |
| 5,194,948 A | 3/1993 | L'Esperance et al. |
| 5,196,006 A | 3/1993 | Klopotek et al. |
| 5,196,027 A | 3/1993 | Thompson et al. |
| 5,201,730 A | 4/1993 | Easley et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat |
| 5,226,903 A | 7/1993 | Mizuno |
| 5,246,435 A * | 9/1993 | Bille et al. .................... 606/6 |
| 5,246,436 A | 9/1993 | Rowe |
| 5,257,988 A | 11/1993 | L'Esperance |
| 5,258,025 A | 11/1993 | Fedorov et al. |

| | | | | | | |
|---|---|---|---|---|---|---|
| 5,263,950 | A | 11/1993 | L'Esperance | 5,476,511 | A | 12/1995 | Gwon et al. |
| 5,263,951 | A | 11/1993 | Spears et al. | 5,480,396 | A | 1/1996 | Simon et al. |
| 5,275,593 | A | 1/1994 | Easley et al. | 5,484,432 | A | 1/1996 | Sand |
| 5,277,911 | A | 1/1994 | Viegas et al. | 5,489,299 | A | 2/1996 | Schachar |
| 5,279,298 | A | 1/1994 | Flower | 5,503,165 | A * | 4/1996 | Schachar .................. 606/4 |
| 5,279,611 | A | 1/1994 | McDonnell et al. | 5,507,740 | A | 4/1996 | O'Donnell, Jr. |
| 5,281,211 | A | 1/1994 | Parel et al. | 5,514,124 | A | 5/1996 | Alpins |
| 5,282,798 | A | 2/1994 | Bruse et al. | 5,514,125 | A | 5/1996 | Lasser et al. |
| 5,284,477 | A | 2/1994 | Hanna et al. | 5,520,679 | A | 5/1996 | Lin |
| 5,288,293 | A | 2/1994 | O'Donnell | 5,527,774 | A | 6/1996 | Girard |
| 5,290,272 | A | 3/1994 | Burstein et al. | 5,529,076 | A | 6/1996 | Schachar |
| 5,295,989 | A | 3/1994 | Nakamura | 5,533,997 | A | 7/1996 | Ruiz |
| 5,300,020 | A | 4/1994 | L'Esperance | 5,556,395 | A | 9/1996 | Shimmick et al. |
| 5,300,061 | A | 4/1994 | Easley et al. | 5,573,544 | A | 11/1996 | Simon et al. |
| 5,300,062 | A | 4/1994 | Ueno | 5,594,753 | A | 1/1997 | Frey et al. |
| 5,300,063 | A | 4/1994 | Tano et al. | 5,618,284 | A | 4/1997 | Sand et al. |
| 5,300,114 | A | 4/1994 | Gwon et al. | 5,627,162 | A | 5/1997 | Gwon et al. |
| 5,304,168 | A | 4/1994 | Sun | 5,632,742 | A | 5/1997 | Frey et al. |
| 5,304,169 | A | 4/1994 | Sand | 5,651,782 | A | 7/1997 | Simon et al. |
| 5,311,224 | A | 5/1994 | Enomoto | 5,656,186 | A | 8/1997 | Mourou et al. |
| 5,312,320 | A | 5/1994 | L'Esperance, Jr. | 5,684,560 | A | 11/1997 | Roffman et al. |
| 5,312,393 | A | 5/1994 | Mastel | 5,709,868 | A * | 1/1998 | Perricone .................. 424/401 |
| 5,314,422 | A | 5/1994 | Nizzola | 5,722,952 | A | 3/1998 | Schachar |
| 5,318,047 | A | 6/1994 | Davenport et al. | 5,731,909 | A | 3/1998 | Schachar |
| 5,318,560 | A | 6/1994 | Blount | 5,738,677 | A | 4/1998 | Colvard et al. |
| 5,323,788 | A | 6/1994 | Silvestrini et al. | 5,752,950 | A | 5/1998 | Frey et al. |
| 5,324,281 | A | 6/1994 | Muller | 5,773,472 | A | 6/1998 | Stjernschantz et al. |
| 5,334,190 | A | 8/1994 | Seiler | 5,828,686 | A | 10/1998 | Frey et al. |
| 5,336,215 | A | 8/1994 | Hsueh et al. | 5,843,184 | A | 12/1998 | Cionni |
| 5,336,216 | A | 8/1994 | Dewey | 5,849,006 | A | 12/1998 | Frey et al. |
| 5,342,351 | A | 8/1994 | Blaha et al. | 5,907,908 | A | 6/1999 | Cunanan et al. |
| 5,342,370 | A | 8/1994 | Simon et al. | 5,980,513 | A | 11/1999 | Frey et al. |
| 5,345,948 | A | 9/1994 | O'Donnell | 6,007,578 | A | 12/1999 | Schachar |
| 5,347,329 | A | 9/1994 | Ota | 6,013,101 | A | 1/2000 | Israel |
| 5,348,551 | A | 9/1994 | Spears et al. | 6,027,494 | A | 2/2000 | Frey |
| 5,350,374 | A | 9/1994 | Smith | 6,055,259 | A | 4/2000 | Frey et al. |
| 5,354,331 | A | 10/1994 | Schachar | 6,059,772 | A | 5/2000 | Hsia et al. |
| 5,356,407 | A | 10/1994 | Easley et al. | 6,099,522 | A | 8/2000 | Knopp et al. |
| 5,356,409 | A | 10/1994 | Nizzola | 6,132,424 | A | 10/2000 | Tang |
| 5,360,424 | A | 11/1994 | Klopotek | 6,190,375 | B1 | 2/2001 | Frey |
| 5,364,388 | A | 11/1994 | Koziol | 6,197,018 | B1 | 3/2001 | O'Donnell, Jr. |
| 5,364,390 | A | 11/1994 | Taboada et al. | 6,197,056 | B1 | 3/2001 | Schachar |
| 5,368,590 | A | 11/1994 | Itoh | 6,233,545 | B1 | 5/2001 | Datig |
| 5,370,641 | A | 12/1994 | O'Donnell | 6,252,595 | B1 | 6/2001 | Birmingham et al. |
| 5,372,595 | A | 12/1994 | Gaasterland et al. | 6,254,595 | B1 | 7/2001 | Juhasz et al. |
| 5,374,265 | A | 12/1994 | Sand | 6,261,220 | B1 | 7/2001 | Frey et al. |
| 5,376,086 | A | 12/1994 | Khoobehi et al. | 6,271,914 | B1 | 8/2001 | Frey et al. |
| 5,391,165 | A | 2/1995 | Fountain et al. | 6,271,915 | B1 | 8/2001 | Frey et al. |
| 5,395,356 | A | 3/1995 | King et al. | 6,280,468 | B1 | 8/2001 | Schachar |
| 5,403,307 | A | 4/1995 | Zelman | 6,299,640 | B1 | 10/2001 | Schachar |
| 5,408,484 | A | 4/1995 | Weimel | 6,302,879 | B1 | 10/2001 | Frey et al. |
| 5,411,501 | A | 5/1995 | Klopotek | 6,312,422 | B1 | 11/2001 | Dubnack |
| 5,412,561 | A | 5/1995 | Rosenshein et al. | 6,312,424 | B1 | 11/2001 | Largent |
| 5,413,555 | A | 5/1995 | McMahan | 6,313,165 | B1 | 11/2001 | Grunberger et al. |
| 5,423,798 | A | 6/1995 | Crow | 6,315,773 | B1 | 11/2001 | Frey et al. |
| 5,423,800 | A | 6/1995 | Ren et al. | 6,319,274 | B1 | 11/2001 | Shadduck |
| 5,423,801 | A | 6/1995 | Muller et al. | 6,322,556 | B1 | 11/2001 | Gwon et al. |
| 5,425,727 | A | 6/1995 | Koziol | 6,324,191 | B1 | 11/2001 | Horvath |
| 5,425,729 | A | 6/1995 | Ishida et al. | 6,325,791 | B1 | 12/2001 | Shimoji |
| 5,425,730 | A | 6/1995 | Luloh | 6,325,792 | B1 | 12/2001 | Swinger et al. |
| 5,437,657 | A | 8/1995 | Epstein | 6,344,040 | B1 | 2/2002 | Juhasz et al. |
| 5,437,658 | A | 8/1995 | Muller et al. | 6,373,571 | B1 | 4/2002 | Juhasz et al. |
| 5,439,462 | A | 8/1995 | Bille et al. | D459,806 | S | 7/2002 | Webb |
| 5,441,496 | A | 8/1995 | Easley et al. | D459,807 | S | 7/2002 | Webb |
| 5,442,412 | A | 8/1995 | Frey et al. | D462,442 | S | 9/2002 | Webb |
| 5,442,487 | A | 8/1995 | Mizuno | D462,443 | S | 9/2002 | Webb |
| 5,445,633 | A | 8/1995 | Nakamura et al. | 6,451,008 | B1 | 9/2002 | Frey et al. |
| 5,460,627 | A | 10/1995 | O'Donnell, Jr. | 6,460,997 | B1 | 10/2002 | Frey et al. |
| 5,461,212 | A | 10/1995 | Seiler et al. | 6,493,151 | B2 | 12/2002 | Schachar |
| 5,462,739 | A | 10/1995 | Dan et al. | 6,494,910 | B1 | 12/2002 | Ganem et al. |
| 5,465,737 | A | 11/1995 | Schachar | 6,497,483 | B2 | 12/2002 | Frey et al. |
| 5,470,329 | A | 11/1995 | Sumiua | 6,585,726 | B2 | 7/2003 | Frey et al. |
| 5,474,548 | A | 12/1995 | Knopp et al. | 6,623,476 | B2 | 9/2003 | Juhasz et al. |

| | | |
|---|---|---|
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Lieberman et al. |
| 6,676,653 B2 | 1/2004 | Juhasz et al. |
| 6,693,927 B1 | 2/2004 | Horvath et al. |
| 6,726,679 B1 | 4/2004 | Dick et al. |
| 6,923,955 B2 | 8/2005 | Till et al. |
| 7,252,662 B2 | 8/2007 | McArdle et al. |
| RE40,420 E * | 7/2008 | Dick et al. ............ 606/4 |
| 2001/0029363 A1 | 10/2001 | Lin |
| 2002/0004658 A1 | 1/2002 | Munnerlyn et al. |
| 2002/0025311 A1 | 2/2002 | Till |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2003/0055412 A1 | 3/2003 | Lieberman et al. |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2004/0054359 A1 | 3/2004 | Ruiz et al. |
| 2004/0070761 A1 | 4/2004 | Horvath et al. |
| 2004/0199149 A1 | 10/2004 | Myers et al. |
| 2005/0107775 A1 | 5/2005 | Huang et al. |
| 2005/0165387 A1 | 7/2005 | Lubatschowski et al. |
| 2006/0195076 A1 | 8/2006 | Blumenkranz et al. |
| 2007/0078447 A1 | 4/2007 | Weinacht et al. |
| 2007/0185475 A1 | 8/2007 | Frey et al. |
| 2007/0265603 A1 | 11/2007 | Pinelli |

OTHER PUBLICATIONS

Ripken, T., et al., "First in-vivo studies of presbyopia treatment with ultrashort laserpulses," Therapeutic Laser Applications and Laser-Tissue Interactions, Proceedings of the SPIE, 2003, pp. 137-145, vol. 5142.
Ripken, T., et al., "Investigations for the correction of presbyopia by fs-laser induced cuts," Ophthalmic Technologies XIV, Proceedings of the SPIE, 2004, pp. 27-35, vol. 5314.
Bellows JG. Cataract and abnormalities of the lens. New York: Grune and Stratton, Inc. 1975:370-372.
Borkman RF, Lerman S. Evidence of a free radical mechanism in aging and UV-irradiated ocular lens, Exp Eye Res. 1977;25:303-309.
Brown N. The change in lens curvature with age. Exp Eye Res. 1974; 19:175-183.
Brown N. The change in shape and internal form of the eye on accommodation. Exp Eye Res. 1973;15:441.
Fischer RF, Presbyopia and the change with age in the human crystalline lens. J Physiol. 1973; 228: 765-779.
Fagerholm PP. The response of the lens to trauma. Trans Ophthalmol Soc UK. 1982;102:369-374.
Farnsworth PN. Anterior zonular shifts with age. Exp. Eye Res. 1979; 28:291-297.
Fisher RF. The elastic constants of the humans lens. J Physiol. 1971; 212:147-180.
Gimbel HV, Beldavs RA. Intrastromal photorefractive keratectomy with the Nd:YLF laser. Int Ophthal Clin. 1994;34(4):139-45.
Gwon A, Fankhauser II F, Puliafito C, Gruber L, Berns M. Focal laser photophacoablation of normal and cataractous lenses in rabbits: Preliminary report. J Cataract Refract Surg. 1995;21:282-286.
Habib M, Speaker M, Kaiser R, Juhasz T. Myopic intrastromal photorefractive keratectomy with the neodymium-Yttrium lithium fluoride picosecond laser in the cat cornea. Arch Ophthalmol. 1995;9:S111-S115.

Hahn DW, Ediger MN, Pettit GH. Dynamics of ablation plume particles generated during excimer laser corneal ablation. Lasers in Surgery and Medicine. 1995;16:384-389.
Juhasz T, Hu XH, Turi L, Bor Z. Dynamics of shock waves and cavitation bubbles generated by picosecond laser pulses in corneal tissue and water. Lasers in Surgery and Medicine. 1994;15:91-98.
Keeney AH. Intraocular foreign bodies. Arch Ophthalmol. 1971;86:499.
Koretz JF, Cook CA, Kuszak JR. The zones of discontinuity in the human lens: development and distribution with age. Vision Res. 1994;34(22)2955-2962.
Koretz JF, Handelman GH, Brown NP. Analysis of human crystalline lens curvature as a function of accommodative state and age. Vision Res. 1984;24(10)1141-1151.
Koretz JF, Handelman GH. Model of the accommodative mechanism in the human eye. Vision Res. 1982;22:917-927.
Koretz JF, Handelman GH. How the human eye focuses. Scientific American. 1988;259: 92-98.
Krueger RR, Quantock AJ, Juhasz T, Ito M, Assil KK, Schanzlin DJ. Ultrastructure of picosecond laser intrastromal photodisruption. Journal of Refractive Surgery. 1996;12:607-612.
Lerman S. Photosensitizing drugs and their possible role in enhancing ocular toxicity. Ophthalmol. 1986; 93(3):304-318.
Lutze M. Lenses of diabetic patients yellow at an accelerated rate similar to older normals. Invest Ophthalmol Vis Sci. 1991; 32:194-199.
Pau H, Kranz J. The increasing sclerosis of the human lens with age and its relevance to accommodation and presbyopia. Graefes Arch for Clin & Exper Ophthalmol. 1991;229(3):294-296.
26. Puliafito CA, Stern D, Krueger RR, Mandel ER. High-speed photography of excimer laser ablation of the cornea. Arch Ophthalmol. 1987;105:1255-9.
Schachar RA. Cause and treatment of presbyopia with a method for increasing the amplitude of accommodation. Ann Ophthalmol. 1992;24:445-452.
Schachar R, Cudmore D, Black T. Experimental support for Schachar's hypothesis of accommodation. Ann Ophthalmol. 1993;25:404-409.
Srinivasan R. Ablation of polymers and biological tissue by ultraviolet lasers. Science. 1986;234:559-565.
Taylor VL, Al-Ghoul KJ, Lane CW, Davis VA, Kuszak JR, Costello MJ. Morphology of the normal humans lens. Invest Ophthal & Vis Sci. 1996;37(7):1396-1410.
Vrensen GF. Aging of the human eye lens—a morphological point of view. Comp Biochem Physiol. 1995;111A:519-532.
Waring GO. Presbyopia and accommodative intraocular lenses-the next frontier in refractive surgery. Ref & Corneal Surg. 1992; 8:421-422.
Werblin TP. Should we consider clear lens extraction for routine refractive surgery- Ref & Corneal Surg. 1992;8:480-48.
Cook CA. Aging of the human crystalline lens and anterior segment. Vision Res 1994;34(22): 2945?2954.
Giblin FJ. Nuclear light scattering, disulfide formation and membrane damage in lenses of older guinea pigs treated with hyperbaric oxygen. Exp Eye Res 1995; 60: 219-235.
Kuszak JR. Lens optical quality is a direct function of lens sutural architecture. Invest Ophthal Vis Sci 1991: 32(7): 2119-2129.
Lim SJ. Analysis of zonular free zone and lens size in relation to axial length of eye with age. J Cat Refract Surg 1998; 24: 390-396.
Schachar RA. Experimental destruction of cataractous lenses by laser. Surg Forum 1973;24: 506-508.
Spector A. Aging of the lens and cataract formation. In: Aging and Human Visual Function. New York. 1982: 27.
Zuclich JA. A comparison of laser induced retinal damage from infrared wavelengths to that from visible wavelengths. Lasers and Light Ophth 1997; 8(1): 15-29.
Brian G & Taylor H. Cataract blindness—challenges for the 21 century. Bulletin of the World Health Organization. 2001 79(3): 249-255.
Bron AJ, Vrensen GFJM, Koretz J, Mariani G, Harding JJ. The Ageing Lens. Ophthalmologica. 2000:214:86-104.
Cromie WJ. Laser makes history's fastest holes. Harvard U Gazette(Internet). Nov. 29, 1999. p. 1-6.

Glasser A, Campbell MCW. Biometric, optical and physical changes in the isolated human crystalline lens with age in relation to presbyopia. Vision Research 1999; 39:1991-2115.

Glasser Adrian, Campbell MCW. On the potential causes of presbyopia(Editorial reply). Vision Research 1999; 39:1267-1272.

Hanson SSRA, Hasan A, Smith DL, Smith JB. The major in vivo modifications of the human water insoluble lens crystallins are disulfide bonds, deamidation, methoionine oxidation and backbone cleavage. Exp Eye Res. 2000;31:195-207.

Al Ghoul KH, Nordgren RK, Kuszak AJ, Freel CD, Costello MJ, Kuszak JK. Structural Evidence of human nuclear fiber compaction as a function of ageing and cataractogenesis. Exp. Eye Res. 2001:72:199?214.

Kuszak JR, Peterson KL, Sivak JG, Herbert KL. The interrelationship of lens anatomy and optical quality II. Primate Lenses. Exp Eye Res. 1994:59:521-535.

Mathias RT, Rae JL, Baldo GJ. Physiological properties of the normal lens. Physiological Review. 1997;77(1)21?50.

Myers RI, Krueger RR. Novel Approaches to Correction of Presbyopia with Laser Modification of the Crystalline Lens,. Journal of Refractive Surgery. 1998;14:36-39.

Sliney DH, Trokel SL. Medical lasers and their safe use. Springer Verlag. New York, 1993. pp. 42?50.

Juhasz T. Kastis GA. et. al. Time resolved observations of shock waves and cavitatin bubbles generated by femtosecond laser pusles in corneal tissue and water. Lasers in Surg & Med. 19:23-31 1996. 62.

Eisner Georg, Eye Surgery—An introduction to operative technique, Springer-Verlag. Berlin 1980. pp. 14-19.

Krueger RR, Surf's Up- Catch a wave with the waterjet. Jrn Ref Surg 14:280-1. 1998.

Kurtz R, Liu X, Elner V, Squier J, Du D, Mourou G, Photodisruption in the Human Cornea as a Function of Laser Pulse Width, Journal of Refractive Surg, vol. 13, Nov./Dec. 1997, p. 653-658.

Intrastromal Photodisruption, http://www.refractivewsource.com/patients/emerging/intrastromal.htm.

Crawford, Kathryn S., et al., "The Role of the Iris in Accomodation of Rhesus Monkeys," Investigative Opthalmalogy & Visual Science, vol. 31, vol. 10, 1990, pp. 2185-2190.

Czygan, G., et al., "Mechanical Testing of Isolated Senile Human Eye Lens Nuclei," Med. Eng. Phys., vol. 18, No. 5, 1996, pp. 345-349.

Datta, Beajyoti, "Tissue Surgery and Subcellular Photodisruption with Femtosecond Laser Pulses," Thesis for Dept. of Physics, Harvard University, 2002, pp. 1-74.

Dausinger, Freidrich, et al., "Micro-maching with Ultrashort Laser Pulses: From Basic Understanding to Technical Application," SPIE, No. 5147, 2002, pp. 1-10.

Douven, Lucen F.A., et al., "Characterisation of Mechanical Behaviour of Human Skin in vivo," SPIE, vol. 3914, 2000, pp. 618-629.

El-Osta, Austen A. R., et al., "In Vitro Model for the Study of Human Posterior Capsule Opacification," J. Cataract Refract Surg. vol. 29, 2003, pp. 1593-1600.

Gayen, Tapan K., et al., "Near-Infrared Laser Welding of Aortic and Skin Tissues and Microscopic Inventigation of Welding Efficacy," SPIE, vol. 4949, pp. 182-185.

Gershenzon, A., et al., "Clinical and Epidemilogy—New Software for Lens Retro-Illumination Digital Image Analysis," Australian and New Zealand Journal of Ophthalmology, 1999, vol. 27, pp. 170-172.

Glasser, Adrian, et al., "On Modeling the Causes of Presbyopia," Vision Research, 2001, vol. 41, pp. 3083-3087.

Glasser, Adrian, et al., "Ultrasound Biomicroscopy of the Aging Rhesus Monkey Cillary Region," Optometry and Vision Science, 2001, vol. 78, No. 6, pp. 417-424.

Grace, Jeffrey M., et al., "Repetitively Pulsed Ruby Lasers As Light Sources for High-Speed Photography," Optical Engineering, vol. 37, No. 8, 1998, pp. 1-26.

Hamaoui, Marie, et al., "Ex-vivo Testing of Crystalline Lens Substitutes: A Pilot Study," SPIE, vol. 3908, 2000, pp. 123-130.

Hartwick, Andrew T. E., et al., "Epithelial Activity of Hexokinase and Glucose-6 Phosphate Dehydrogenase in Cultured Bovine Lenses Recovering from Pharmaceutical-Induced Optical Damage," Molecular Vision, vol. 9, 2003, pp. 594-600.

Heisterkamp, Alexander, et al., "Nonlinear Effects Inside Corneal Tissue after FS-Photodisruption," SPIE, vol. 4433, 2001, pp. 55-60.

Ho, A., et al., "Feasibility of Simultaneous Correction of Ametropia by Varying Gel Refractive Index with Phaco-Ersatz," SPIE, vol. 4245, 2001, pp. 119-128.

Holzer, Mike P., et al., "Corneal Flap Complications in Refractive Surgery—Part 1: Development of an Experimental Animal Model," J. Cataract Refract Surg, vol. 29, 2003, pp. 795-802.

Holzer, Mike P., et al., "Corneal Flap Complications in Refractive Surgery—Part 2: Postoperative Treatments of Diffuse Lamellar Keratitis in an Experimental Animal Model," J. Cataract Refract Surg, vol. 29, 2003, pp. 803-807.

Akchurin, Gairf, et al., "Evaluation of the degree of turbidity of cataract lens and its correlation with retinal visual acuity," SPIE, vol. 3591, 1999, pp. 74-81.

Amann, Josef, et al., "Increased Endothelial Cell Density in the Paracentral and Peripheral Regions of the Human Cornea," American Journal of Ophthalmology, vol. 135, No. 5, 2003, pp. 584-590.

Amendt, M. Strauss, et al., "Modeling of Bubble Dynamics in Relation to Medical Applications," SPIE, vol. 2975, 1997, pp. 362-373.

Ansari, Rafat R., et al., "Measuring Lens Opacity: Combining Quasi-Elastic Light Scattering With Scheimpflug Imaging System," SPIE, vol. 3246, 1998, pp. 35-42.

Apple, David J., et al., "Preparation and Study of Human Eyes Obtained Postmortem with the Miyake Posterior Photographic Technique," Ophthalmology, vol. 97, No. 6, 1990, pp. 810-816.

Barak, Adiel, et al., "Anterior Capsulotomoy Using the CO2 Laser," SPIE, vol. 3246, 1998, pp. 196-198.

Balaram, Mini, et al., Noncontact Specular Microscopy of Human Lens Ephitelium, IOVS, vol. 41, No. 2., 2000, pp. 474-481.

Ben-Sira, I., et al., "Clinical Method for Measurment of Light Backscattering from the in vivo human lens," Invest. Ophthalmology Vis, Sci., vol. 19, No. 4 (Reports), 1980, pp. 435-437.

Benjamin, William J., "Borish's Clinical Refraction," W. B. Saunders, publishers, copyright 1998, p. 110.

Bettelheim, Frederick A., et al., "Syneretic Response of Aging Normal Human Lens to Pressure," Investigative Ophthalmology & Visual Science, Vo. 44, No. 1, 2003, pp. 258-263.

Bito, L.Z., et al., "Age-Dependent Loss of Accomodative Amplitude in Rhesus Monkeys: An Animal Model for Presbyopia," Invest. Ophthalmol. Vis. Sci., vol. 23, No. 1, 1982, pp. 23-31.

Breitling, Detlef, et al., "Fundamental Aspects in Machining of Metals with Short and Ultrashort Laser Pulses," SPIE, vol. 5339, pp. 1-15.

Burd, H.J., et al., "Numerical Modeling of the Accommodating Lens," Vision Research, vol. 42, 2002, pp. 2235-2251.

Carey, James, et al., "Propogation and Characterization of Ultrashort Laser Pulses," Spectroscopy of Systems with Spatially Confined Structures, Ed. Rino Di Bartolo, Kluwer Academic Press, Netherlands, 2003, pp. 1-30.

Chen, Wei-Li, et al., "Ultrasound Biomicroscopic Findings in Rabbit Eyes Undergoing Scleral Suction during Lamellar Refractive Surgery," IOVS, vol. 43, No. 12, 2002, pp. 3665-3672.

Clafin, E.S., et al., "Configuring an Electrostatic Membrane Mirror by least-squares fitting with analytically derived influence functions," J. Opt. Soc. Am. A., vol. 3, No. 11, 1986, pp. 1833-1839.

Coleman, D. Jackson, et al., "Presbyopia, Accommodation, and the Mature Catenary," Ophthalmology, vol. 108, No. 9, 2001, pp. 1544-1551.

L'Esperance, Jr., Opthalmic Lasers Photocoagulation, Photoradiation and Surgery, 2nd Ed., copyright 1983, The C. V. Mosby Company, pp. 529-538.

Liu, Xinbing, et al., "In vivo Plasma-mediated Ablation as a Function of Laser Pulsewidth," SPIE, vol. 2975, 1997, pp. 282-288.

Loerscher, Hanspeter, et al., "Noncontact Trephination of the Cornea Using a Pulsed Hydrogen Floride Laser," American Journal of Ophthalmology, vol. 104, pp. 471-475.

Loesel, Frieder H., et al., "Laser-Induced Optical Breakdown on Hard and Soft Tissues and its Dependence on the Pulse Duration: Experiment and Model," IEEE Journal of Quantum Electronics, vol. 32, No. 10, 1996, pp. 1717-1722.

Masters, B.R., "Three Dimensional Microscopic Tomographic Imaging of the Cataract in a Human Lens In Vivo," Optics Express, 332, vol. 3, No. 9, 1998, pp. 332-338.

Mathias, R.T., et al., "Physiological Properties of the Normal Lens," Physiological Review, vol. 77, No. 1, 1997, pp. 21-50.

Michael, Ralph, et al., "Refractive Index of Lens Fiber Membranes in Different Parts of the Crystalline Lens," Proceedings of SPIE, Vo. 4611, 2002, pp. 159-164.

Marion II, John E., et al., "Medical Applications of Ultra-Short Pulse Lasers," SPIE, vol. 3616, 1999, pp. 42-50.

Moffat, B. A., et al., "Age-Related Changes in Refractive Index Distribution and Power of the Human Lens as Measured by Magnetic Resonance Micro-Imaging in Vitro," Vision Research, vol. 42, 2002, pp. 1683-1693.

Neev, Joseph, "Ultrashort Pulse Lasers: A New Tool for Biomedical Applications," SPIE, Vo. 3255, pp. 2-7.

Oberheide, Uwe, et al., "Therapy Monitoring of Laser Cyclophotocoagulation," Proceedings of SPIE, vol. 4611, 2002, pp. 48-53.

Oriowo, Olanrewaju Matthew, "A Study of Ultraviolet Radiation Effects on Procine Crystalline Lens and Development of a New Assay Methodology for UV Cataractogensis Inivestigation," A Thesis Presented to the University of Waterloo, 2000, pp. i-xix and 1-218.

Parel, Jean Marie, et al., "Intraocular Implants for the Surgical Correction of Presbyopia," In Opthalmic Technologies X, Proceedings of SPIE, vol. 3908, 2000, pp. 115-122.

Payne, Peter A., et al., "Ophthalmic Applications of Laser-Generated Ultrasound," SPIE, vol. 3908, 2000, pp. 13-22.

Peterson, Jennifer A., et al., "Intraocular Pressure Measurement in Cynomolgus Monkeys, Tono-Pen Versus Manometry," Investigative Opthalmology & Visual Science, 1996, vol. 37, No. 6, pp. 1197-1199.

Fleck, et al., "Q-switched ND:YAG Laser Distruption of Rabbit Lens Nucleus," Lasers and Light in Opthamology, vol. 3, No. 3, pp. 227-232 (1990).

Cook, Christopher A., et al., "Aging of the Human Crystalline Lens and Anterior Segment," Vision Res., vol. 34, No. 22, pp. 2945-2954, 1994.

Koretz, Jane F., et al. "The Zones of Discontinuity in the Human Lense: Development and Distribution with Age," Vision Res., vol. 34, No. 22, pp. 2955-2962, 1994.

Qian, Wen, et al., "3 Year Simvastatin Treatment and Lens Nuclear Back Scattering," J. Ophthalmol, vol. 84, 2000, pp. 512-516.

Qian, Wen, et al., "Universal Opacity Standard for Scheimpflug Photography," Ophthalmic Res, 2000, vol. 32, pp. 292-298.

Rockewll, B. A., et al., "Safe Use of Ultrashort Lasers," SPIE, vol. 3616, 1999, pp. 32-39.

Roi, Pascal, et al., "An Optomechanical Eye Model for Observation of Lens Photoablation," SPIE, 1997, vol. 2971, pp. 171-174.

Sacks, Zachary S., et al., "Laser Spot Size as a Function of Tissue Depth and Laser Wavelength in Human Sclera," SPIE, 1998, vol. 3255, pp. 67-76.

Scammon, Richard J., et al., "Simulations of Shock Waves and Cavitation Bubbles Produced in Water by Picosecond and Nanosecond Laser Pulses," SPIE, 1998, vol. 3254, pp. 264-275.

Schachar, Ronald A. MD, et al., "Mechanism of Human Accommodations as Analyzed by Nonlinear Finite Element Analysis," Ann. Opthalmol, 2001, vol. 33, No. 2, pp. 103-112.

Schaeffel, Frank, "Kappa and Hirschberg Ration Measured With an Automated Video Gaze Tracker," Optometry and Vision Science, 2002, vol. 79, No. 5, pp. 329-334.

Schaffer, Chris B., et al., "Dynamics of Femtosecond Laser-Induced Breakdown in Water From Femtoseconds to Microseconds," Optics Express, 2002, vol. 10, No. 3, pp. 196-203.

Shen, Nan, "Photodisruption in Biological Tissues Using Femtosecond Laser Pulses," A Thesis Presented to the Department of Physics, Harvard University, 2003, pp. 1-125.

Sher, Neal A. MD, "Hyperopic Refractive Surgery," Current Opinion in Ophthalmology, 2001, vol. 12, pp. 304-308.

Söderberg, Per G., et al., "Angular Dependence of the Intensity of Back Scattered Light From Human Lenses with Nuclear Cataract, Implications for Measurement," SPIE, 2000, vol. 3908, pp. 34-37.

Garner, LF, et al., "Changes in Equivalent and Gradient Refractive Index of the Crystalline Lens with Accommodation," Optom Vis Sci, 1997, 74(2): 114-9, 1 pg.

Garner, LF, et al., "Changes in Ocular Dimensions and Refraction with Accommodation," Opthalmic Physiol. Opt., 1997, 17(1): 12-7, 1 pg.

McBrien, NA, et al., "Experimental Myopia in a Diurnal Mammal (Sciurus Carolinesis) with No Accommodative Ability," J. Physiol., 1993, 469:421-41, 1 pg.

McCourt, ME, et al., "Refractive State, Depth of Focus, and Accommodation of the Eye of the California ground squirrel (Spermophiliu beecheyi)" Vision Res., 1984, 24(10):1261-6, 1 pg.

Prokofeva, GL, et al., "Effects of Low-Intensity Infrared Laser Irradiation on the Eye An Experiemental Study," Vestn Oftalmol, 1996, 112(1):31-32, 1 pg.

Avro, "Statement of the Use of Animals in Opthalmic and Visual Research," The Association for Research in Vision and Opthalmology, copyright © 2002, obtained from the Internet on Jan. 15, 2005 at http://www.avro.org/AboutAvro/anamlst.asp, 3 pgs.

Söderberg, Per G., et al., "External Standard for Measurements with the Scheimpflug Slitlamp Microscope," SPIE, 1997, vol. 2971, pp. 8-13.

Stilzel, Joel D., et al, "A Nonlinear Finite Element Model of the Eye with Experimental Validation for the Prediction of Globe Rupture," Stapp Car Crash Journal, 2002, vol. 45, 24 pgs.

Strauss, Moshe, et al., "Two-Dimensional Rayleigh Model of Vapor Bubble Evolution," SPIE, 1999, vol. 3601, pp. 212-224.

Strenk, Susan A., et al., "Age-Related Changes In Human Ciliary Muscle and Lens: A Magnetic Resonance Imaging Study," Investigative Ophthalmology & Visual Science, 1999, vol. 40, No. 6, pp. 1162-1169.

Sweeney, Matthew H. J., et al., "Movement of Cysteine in Intact Monkey Lenses: The Major Site of Entry is the Germinative Region," Experimental Eye Research, 2003, vol. 77, pp. 245-251.

Tahi, Hassan, et al., "Restoring Accommodation: Surgical Technique and Preliminary Evaluation in Rabbits," SPIE 1999, vol. 3591, pp. 267-269.

Tang, Daxin, "Influence of Age, Diabetes and Cataract on Calcium, Lipid-Calcium and Protein- Calcium Relationships in Human Lenses," Investigative Ophthalmology & Visual Science, 2003, vol. 44, No. 5, pp. 2059-2066.

Vilupuru, Abhiram S., "Optical and Biometric Relationships of the Isolated Pig Crystalline Lens," Ophthal. Physiol. Opt., 2001, vol. 21, No. 4, pp. 296-311.

Vogel, Alfred, et al., "Interaction of Laser-Produced Cavitation Bubbles with Elastic Tissue Model," SPIE, 2001, vol. 4257, pp. 167-177.

Vogel, Alfred, et al., "Numerical Simulation of Optical Breakdown for Cellular Surgery at Nanonsecond to Femtosecond Time Scales," SPIE, 2001, vol. 4433, pp. 70-80.

Vogel, Alfred, et al., "Laser-Induced Breakdown in the Eye at Pulse Durations from 80 ns to 100fs," SPIE, 1998, vol. 3255, pp. 34-49.

Vogel, Alfred, et al., "Kinetics of Phase Transitions in Pulsed IR Laser Ablation of Biological Tissues," SPIE, 2003, vol. 4961, pp. 66-74.

Fisher, R F, "The Ciliary Body in Accommodation," Trans. Opthalmol Soc. UK, 1989, 105 (Pt2): 208-19, 1 pgs. abstract only.

Fisher, R F, "The Mechanics of Accommodation in Relation to Presbyopia," Eye, 1988, 2 (Pt6): 646-9-1 pg. abstract only.

Juhasz, T., et al., "Time-Resolved Studies of Plama-Mediated Surface Ablation of Soft Biological Tissue with Near-Infrared Picosecond Laser Pulses," SPIE, vol. 2975, 1997, pp. 271-281.

Kasthurirangan, Sanjeev, "Amplitude Dependent Accommodative Dynamics in Humans," Vision Research, vol. 43, 2003, pp. 2945-2956.

Koopmans, Steven A., et al., "Polymer Refilling of Presbyopic Human Lenses in Vitro Restores the Ability to Undergo Accommodative Changes," IOVS, vol. 44, No. 1, 2003, pp. 250-257.

Krag, Susanne, "Biomechanical Measurements of the Lens Capsule," Scandinavian University Thesis, 1999.

Krag, Susanne, et al., "Mechanical Properties of the Human Posterior Lens Capsule," IOVS, vol. 44, No. 2, 2003, pp. 691-696.

Krauss, Joel, et al., "Laser Interactions with the Cornea," Survey of Ophthalmology A167, vol. 31, No. 1, 1986, pp. 37-53.

Krueger, Ronald R., et al, "Experimental Increase in Accommodative Potential After Neodymium: Yttrium-Aluminum-Gamet Laser Photodisruption of Paired Cadaver Lenses," Ophthalmology vol. 108. No. 11, 2001, pp. 2122-2129.

Kuizenga, Dirk J., "FM-Laser Operation of the Nd:YAG Laser," IEEE Journal of Quantum Electronics, vol. 6, No. 11, 1970, pp. 673.

Kurtz, Ron, et al., "Femtosecond Laser Corneal Refractive Surgery," SPIE, vol. 3591, 1999, pp. 209-219.

Kurtz, Ron, et al., "Ophthalmic Application of Ferntosecond Lasers," SPIE, vol. 3616, 1999, pp. 51-65.

Kurtz, Ron, et al. "Optimal Laser Parameters for Intrastromal Corneal Surgery," SPIE, vol. 3255, 1998, pp. 56-66.

Kuszak, J.R., et al., "A Quantitative Analysis of Sutural Contributions to Variability in Back Vertex Distance and Transmittance in Rabbit Lenses as a Function of Development, Growth and Age," Optometry and Vision Science, vol. 73, No. 3, 2002, pp. 193-204.

Kuszak, J. R., et al., "Electron Microscope Observations of the Crystalline Lens," Microscopy Research and Technique, 1996, vol. 33, pp. 441-479.

Kuszak, J.R., et al., "Quantitative Analysis of Animal Model Lens Anatomy: Accommodative Range is Related to Fiber Structure and Organization," Dept. of Ophthalmology and Pathology, undated, 26 pgs.

Kuszak, J. R., et al., "Suppression of Post-Vitrecetomy Lens Changes in The Rabbit by Novel Benzopyranyl Esters and Amides," Exp. Eye Res., vol. 75, 2002, pp. 459-473.

Kuszak, J. R., et al., "The Relationship Between Rabbit Lens Optical Quality and Sutural Anatomy after Vitrectomy," Exp. Eye Res., vol. 71, 2000, pp. 267-281.

Braham, Lewis, "Eye Surgery: It's Getting Sharper", Business Week, Oct. 18, 2004, p. 142, 145.

Aston, Adam, "Why Settle for 20/20?", Business Week, Mar. 17, 2003, p. 95-96.

* cited by examiner

ANTERIOR → POSTERIOR

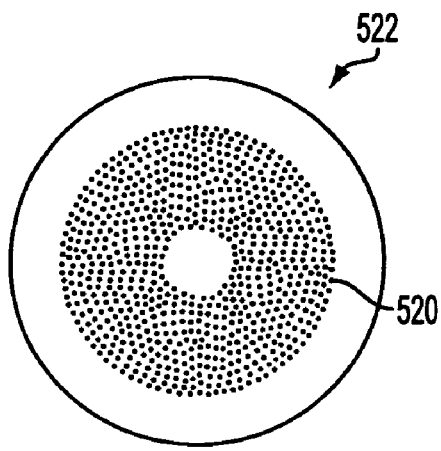 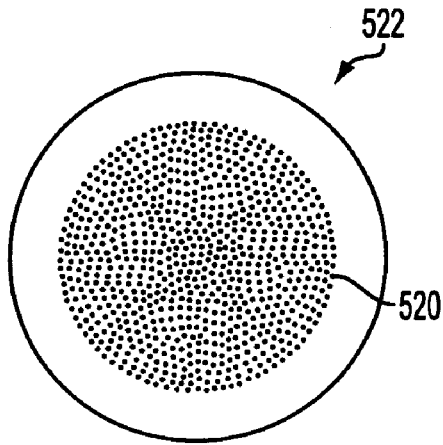
FIG. 5A  FIG. 5B
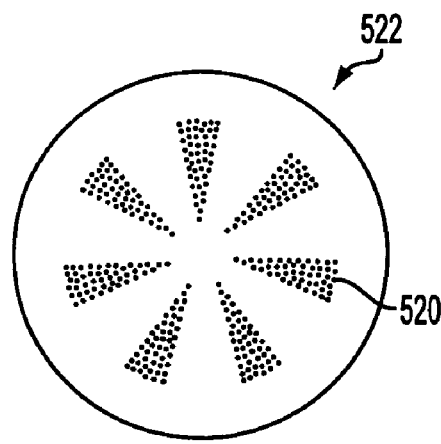 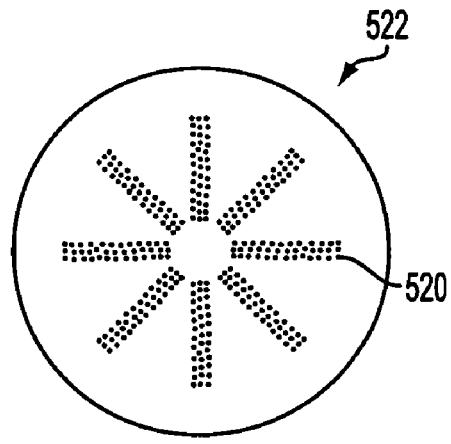
FIG. 5C  FIG. 5D
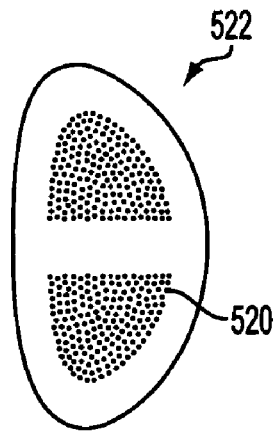
FIG. 5E

LENTICULAR REFRACTIVE SURGERY OF PRESBYOPIA, OTHER REFRACTIVE ERRORS, AND CATARACT RETARDATION

CROSS REFERENCE TO RELATED APPLICATIONS

The application claims benefit to and is a Continuation-in-Part of U.S. patent application Ser. No. 09/897,585 filed Jun. 29, 2001, now abandoned, which is a Continuation of U.S. patent application Ser. No. 09/312,518, filed May 14, 1999, now abandoned, which in turn is a Continuation of U.S. patent application Ser. No. 08/821,903, filed Mar. 21, 1997, now abandoned, which claims priority to U.S. Provisional Application No. 60/036,904, filed Feb. 5, 1997, and U.S. Provisional Application No. 60/013,791, filed Mar. 21, 1996.

BACKGROUND

1. Field of Invention

The invention comprises the use of electromagnetic energy to make physical and biochemical alterations to the ocular lens of a mammalian eye for the correction of visual impairments, particularly presbyopia and including other ametropias such as myopia, hyperopia and regular and irregular astigmatism, and the retardation of cataract development.

2. Description of Related Art

Vision impairment is an exceedingly common problem in humans. Nearly 100% of people over age 50 have some form of vision impairment. The need for corrected vision (e.g., the need for glasses or contacts) is also very common among younger people. In a vast majority of people needing vision correction the problem is associated with the crystalline lens of the eye. Two primary problems that occur in the crystalline lens are (a) insufficient flexibility resulting in the inability to correctly focus incoming light and (b) light scattering also resulting in blurred vision.

The common errors of focusing of the eye fall into a class of visual impairments termed ametropias, which include myopia, hyperopia, astigmatism (regular and irregular) and presbyopia. These impairments generally cause visual blurring, and are most commonly corrected with eyeglasses or contact lenses, and sometimes with surgery. Myopia is the ocular condition where light from a distant object focuses in front of the retina resulting in blurred distance vision, while visual images of near objects are generally clear. Myopia is the most common reason for vision correction in a population under age 30. In hyperopia, an image of a distant object is focused behind the retina, making distance and near vision blurred, except where described later. Hyperopia, although exceedingly common, is not normally corrected until the fortieth decade when presbyopia makes correction necessary. Astigmatism is a refractive error that results in the eye's inability to focus along a first axis in a plane perpendicular to the line of sight being different from the eye's ability to focus along a second axis in the same plane perpendicular to the first axis, thus producing an image incapable of focusing at any distance. Astigmatism generally occurs as a second impairment along with either myopia or hyperopia, but is occasionally the only reason for needing visual correction. Astigmatism is subdivided by type and includes regular and irregular astigmatism as well as aberration. In irregular astigmatism there are other distortions or aberrations which are in some persons corrected by considering its effect upon the wavefront function. The wavefront function characterizes the refractive profile of the eye and defines irregular astigmatism, which is considered a higher order optical aberration such as spherical aberration, coma, trifoil, and others often characterized by Zernicke polynomials above the fourth order. (See, for example, Rae, Krueger & Applegate, *Customized Corneal Ablation* (2001), which is specifically incorporated herein by reference).

Of the ametropias, presbyopia stands out as a significant problem because of its prevalence and because it is not corrected as successfully as are myopia and hyperopia with the current treatment methods. Presbyopia is the focusing error caused by a loss of flexibility of the ocular lens. Lens flexibility allows for accommodation, which is the primary mechanism by which the eye changes focus. Accommodation is the change in shape of the ocular lens as it responds to neural feedback, ideally to focus light precisely on the back of the retina, allowing the perceived image to be seen in sharp focus. Presbyopia generally causes clinically significant blurred vision in humans starting between the ages of 40 and 50 years, and is one of the few human disorders with a prevalence of 100% in the population that reaches the age of the mid-50's.

Functionally, loss of accommodation is a life long process through which the ability of the ocular lens to change shape to allow for focused vision continually decreases starting essentially at birth. This change is evidenced in the following typical data comparing the eye's focusing ability, here measured by the eye's shortest focal length in units of diopters (the reciprocal of focal length measured in meters) to the age of an eye: 14 D. (focal length at 7 cm) at 10 years; 8.00 D. (f=12.5 cm) at 30 years, 4.00 D. (f=25 cm) at 45 years, and 1.00 D. (f=100 cm) at 52 years.

Until absolute presbyopia (i.e., no accommodation) occurs, focusing on close objects is achieved through the control of the ciliary muscle. Two theories of how this occurs have coexisted for more than 100 years, and have only recently been clarified by direct observation with sophisticated cameras and ultrasound systems. The Helmholz theory first proposed in 1909 basically defines the crystalline lens as being held in resting tension by the ciliary muscle when the lens is focused for a distance object. When the lens focuses on nearer objects, it is through the relaxation of the ciliary muscle, and releasing of any tension on the lens, yielding a thicker or more convex lens.

In addition to presbyopia, it is well known that another process occurs within the ocular lens throughout a normal human life that also generally becomes clinically diagnosable during the fourth decade of life. This second degenerative process manifests as the scattering of light as it passes through the lens. The process that leads to light scattering is the first step to cataract development.

Cataracts are areas of opacification of the ocular lens of sufficient size to interfere with vision. They have been extensively studied because of their high prevalence in a geriatric population. Cataracts in the aged (senile cataracts) are the most common type, and are often thought to be due to an acceleration of the previously mentioned light scatter. Cataracts occur to varying extents in all humans over the age of 50 years, but generally do not cause significant visual dysfunction until the ages of 60-80 years. Cataracts, however, can occur much earlier as a result of risk factors including disease, trauma, and family history.

FIG. 2 is presented as an aid to understanding the visual impairments related to the ocular lens (3). The ocular lens (3) is a multi-structural system as illustrated in FIG. 2. The macroscopic lens structure includes a cortex (13) just inside a capsule (14), which is an outer membrane that envelopes the other interior structures of the lens. The nuclei are formed from successive additions of the cortex (13) to the nuclear regions, which are subdivided into a deep fetal nucleus (22), which develops in the womb, an infantile nucleus (24), a juvenile nucleus (26), and the adult nucleus (28). On the microscopic level the structure of the nuclei is layered, resembling the structure of an onion with the oldest layers and oldest cells towards the center. Rather than being spherical, the lens is a biconvex shape as shown in FIG. 2. The cortex and the different nuclei have specific structures that are consistent through different ages for specific cell sizes, compactions, and clarity. The lens epithelium (23) forms at the lens equatorial region (21) generating ribbon-like cells or fibrils that grow anteriorly and posteriorly around the ocular lens. The unique formation of the crystalline lens is the biconvex shape where the ends of the cells align to form a suture in the central and paracentral areas both anteriorly and posteriorly. Transparency is maintained by the regular architecture of the fibrils. As long as the regular architecture is maintained, light passes unobstructed through the lens. The older tissue in both the cortex and nucleus has reduced cellular function, having lost their cell nuclei and other organelles several months after cell formation. The aqueous (17), the liquid in the anterior chamber between the lens and cornea flows very slowly through the lens capsule (14) and the sutures into more remote areas of the lens and provides the nutrients needed for minimal cellular life functions, including the removal of toxic and oxidative byproducts.

The microstructure of the fibrils contains interconnections between the ribbon-like fibrils called balls and sockets and interdigitations and imprints, which to some extent inhibit the relative motion of fibrils with respect to one another. Still, the fibrils are relatively free to move in relation to each other in the young, flexible crystalline lens. As the eye ages, there are age related changes to these structures that include the development of intermolecular bonding, mostly disulfide bonding, the compaction of tissue, the breakdown of some of the original attachments, and the yellowing or darkening of older lens areas.

Changes in the size and shape of the macroscopic lens components throughout life include both the increased curvature and general enlargement of the biconvex lens with age. The thickness of the posterior portion increases more than the anterior portion. Additionally, thickness increases are proportionately greater in the periphery.

The above mentioned disulfide bonding immobilizes the oldest and deepest lens tissue, characteristically seen in the nuclear regions. However, disulfide bonds are weak chemical bonds, and are subject to modification and breakage with relatively little energy. The disulfide bonds are largely formed by the effects of ambient ultraviolet (UV) light from the atmosphere and from the continual, unrelenting reduction in lens movement with age (presbyopia). The lens absorbs fluids from the aqueous, a process enhanced by lens accommodation, e.g., the undulating movement of the younger crystalline lens. The aqueous normally contains antioxidants that aid in preventing disulfide bond formation that further inhibits lens movement.

Just as for the mechanism of presbyopia, light scattering and cataractogenesis results from interfibril attachment. On the cellular level, all cataracts begin with oxidative changes of the crystalline tissue. The changes in the lens tissue that lead to light scattering occur when individual fibers combine to form large, light-disrupting macromolecular complexes.

The two different processes that lead to presbyopia and light scattering occur simultaneously and continuously but at different rates. The possible connection between the two processes was clarified by a 1994 report by Koretz et al. (Invest. Ophthal. Vis. Science (1994)), the entirety of which is specifically incorporated herein by reference to the extent not inconsistent with the disclosures of this patent. Koretz et al. studied extensively the presence of zones of light scatter. They not only confirmed that older lenses had more light scatter, but also they reported an acceleration in the rate of formation of light-scattering macromolecular complexes starting in the fourth decade of life. Since certain natural antioxidants within the lens are known to counteract the changes that produce light scatter, Koretz theorized that reduced lens movement due to decreased accommodation reduces the flow of fluids carrying the antioxidants and thereby exacerbates the process leading to light scattering.

As further foundation for this discussion, the anatomical structures of the eye are shown in FIG. 1, a cross sectional view of the eye. The sclera (31) is the white tissue that surrounds the lens except at the cornea. The cornea (1) is the transparent tissue that comprises the exterior surface of the eye through which light first enters the eye. The iris (2) is a colored, contractible membrane that controls the amount of light entering the eye by changing the size of the circular aperture at its center (the pupil). The ocular or crystalline lens (3), a more detailed picture of which is shown in FIG. 2, is located just posterior to the iris. Generally the ocular lens changes shape through the action of the ciliary muscle (8) to allow for focusing of a visual image. A neural feedback mechanism from the brain allows the ciliary muscle (8), acting through the attachment of the zonules (11), to change the shape of the ocular lens. Generally, sight occurs when light enters the eye through the cornea (1) and pupil, then proceeds past the ocular lens (3) through the vitreous (10) along the visual axis (4), strikes the retina (5) at the back of the eye, forming an image at the macula (6) that is transferred by the optic nerve (7) to the brain. The space between the cornea and the retina is filled with a liquid called the aqueous in the anterior chamber (9) and the vitreous (10), a gel-like, clear substance posterior to the lens.

The traditional solution for the correction of presbyopia and other refractive errors is to provide distance glasses, reading glasses, or a combination of the two called bifocals. Other forms of correction include the following: a) variable focus bifocal or progressive spectacles, b) contact lenses, c) aspheric corneal refractive surgery, and d) intraocular implant lenses for aphakic (absence of the ocular lens) individuals. Bifocal contact lenses are uncommonly used because, for fitting or for technical reasons, they are optically inferior to bifocal spectacles. An additional corrective method using contact lenses called "monovision" corrects one eye for near and the other for far, and the wearer learns to alternate using each eye with both open. Aspheric photorefractive keratectomy (such as is described in Ruiz, U.S. Pat. No. 5,533,997 and King, U.S. Pat. No. 5,395,356, the entire disclosures of which are specifically incorporated herein by reference to the extent not inconsistent with the disclosures of this patent) provides variable focus capabilities through an aspheric reshaping of the cornea. Similar to this optical correction, some aspherical intraocular implant lenses take the place of the natural ocular lens in individuals whose lens has been removed during cataract surgery. All of these techniques have one or more of the following disadvantages: a) they do not have the continuous range of focusing that natural accommodation provides; b) they are external devices placed on the face or eye; or c) they cut down the amount of light that normally focuses in the eye for any one particular distance, a particular problem because middle-aged individuals actually need more light because of light loss due to the development of light scattering, as described above.

Further treatments founded on using nutritional supplements have been considered to enhance accommodation and retard cataract development. Additionally, behavioral optometrists proposed many years ago the use of focusing exercises to slow down the deterioration of lens accommodation. None of these treatments has been widely accepted.

Alternative treatment methods to glasses have been more successful in correcting such refractive errors as myopia (nearsightedness), hyperopia (farsightedness), and astigmatism compared with their limited success in treating presbyopia. Such alternative treatments use photorefractive procedures in an attempt to correct refractive errors and avoid the necessity of external lenses (e.g., spectacles and contact lenses), including the currently FDA-approved procedures of photorefractive keratectomy (PRK) and laser-assisted keratomileusis (LASIK). PRK and LASIK treatments use a laser to produce a unique shape in the static cornea of the eye that is calculated to precisely focus light at the retina taking into account the dimensions and limitations of other structures of the eye, especially the crystalline lens. These procedures are of limited utility specifically because they treat the static cornea and do not account for the dynamics of the crystalline lens, which change over time as evidenced by the occurrence of presbyopia.

Another disadvantage of the present photorefractive procedures is that they generally involve fairly invasive surgery. For instance, LASIK requires an incision in the cornea to create a flap of tissue that is peeled back to expose the interior of the cornea, which is then precisely sculpted to focus light on the retina.

For presbyopic correction specifically, current methods generally require surgical incision and physical penetration of a portion of the eye. For instance, Werblin (U.S. Pat. No. 5,222,981) proposed the surgical removal of the clear, intact crystalline lens for the purpose of correcting presbyopia and other ametropias, and substituting a multiple interchangeable components-intraocular lens. Removal of the lens requires an incision through which it can be removed.

Another development in photorefractive treatment of presbyopia is Bille (U.S. Pat. No. 4,907,586), which primarily describes a quasi-continuous laser reshaping the eye, namely the cornea and secondarily the crystalline lens in order to correct myopia, hyperopia, and astigmatism. Bille, however, also proposed that presbyopia might be corrected by semi-liquification or evaporation of lens tissue through treatment with a quasi-continuous laser.

In WO95/04509 and again later in U.S. Pat. No. 6,322,556, Gwon described a method to correct presbyopia, myopia, and hyperopia with an ultrashort laser pulse that produced volumetric reductions of lens tissue. While various methods to replace the clear crystalline lens with a flexible or gel intraocular implant have been developed as an alternate lenticular technology, Gwon's patented method was the only major milestone in direct treatment of the natural lens.

Scleral expansion is a presbyopia treatment method proposed in patents by Schachar (U.S. Pat. Nos. 5,529,076, 5,503,165, 5,489,299, and 5,465,737). In these patents, Schachar discloses a method of stretching the sclera, which restores accommodation by shifting the attachment of the cilliary muscle, allowing the lens to stretch its diameter. In addition, he suggests an alternative embodiment involving the use of laser irradiation of the lens to destroy the germinal epithelium to remove the source of growth of the crystalline lens. Schachar's method has been described to work according to the Tscherning mechanism, an alternative mechanism to the Helmholz theory and is an example of the multiplicity of presbyopia theories present in the field through the late 1990s.

Development of crystalline lens modification technology and presbyopia correction specifically may have been slow after 1990 because the Bille patent was directed (as was other research in the field) primarily toward the cornea, a simpler system than the dynamic crystalline lens because it a static refractive surface.

Another reason that crystallin lens modification technology has developed slowly is that ophthalmic professionals are accustomed to wholly removing the crystalline lens during cataract surgery, the most commonly performed surgery in the United States (greater than one million per year). Modifying the crystalline lens is considered the antithesis of the prevailing thought about lens removal. Also, ophthalmic professionals have traditionally looked upon the crystalline lens as susceptible to cataract development from a wide variety of causes especially trauma such as that of surgery directly on this tissue. A summary consisting of sixty-nine pages in Davson's *The Eye* (1980), illustrates the wide breadth of causes of cataracts in the crystalline lens, including ultraviolet, infrared, and ultrasound energy; incisional surgery from the anterior (e.g., cornea) or the posterior (e.g., retina); many systemic diseases including diabetic changes from hyper- to hypo-glycemic conditions; trauma; toxic chemicals and pharmacological drugs; and malnutrition and vitamin deficiencies.

A reason that laser surgery is of particular interest is that much of the ocular media is transparent to the visible light spectrum, i.e., wavelengths of 400-700 nanometers (nm); thus, light of wavelengths in this range pass through the anterior eye without effect. While the near-visible spectrum on either side of the visible range, including ultraviolet and infrared light, has certain absorptive characteristics in various ocular tissues and may cause changes in the tissue, the safety of light irradiation can be specified according to a threshold energy level below which particular tissues will not be adversely affected. Above the threshold, ultraviolet or infrared light can cause damage to the eye, including the establishment of cataracts or even tissue destruction. The ability to destroy ocular tissue, however, can be made to be quite beneficial, and is a major premise underlying eye surgeries using light energy. As described below, light energy can be focused to a specific point, where the energy level at that point (expressed as a energy density) is at or above the threshold for tissue destruction. Energy in the light beam prior to focusing can be maintained at a energy density below the threshold for tissue destruction. This "pre-focused" light can be referred to using the term subthreshold bundles (described by L'Esperance, U.S. Pat. No. 4,538,608, the entire disclosure of which is specifically incorporated herein by reference to the extent not inconsistent with the disclosures of this patent), wherein the "bundles" are not destructive to tissue.

Lasers have been used widely to correct many ocular pathological conditions, including the suppression of hemorrhaging, the repair of retinal detachments, the correction of abnormal growth of the lens capsule after cataract surgery (posterior capsulotomy), and the reduction in intraocular pressure. Therefore, various laser sources providing numerous and even continuously variable wavelengths of laser light are well know in the art. The characteristics of the laser, including its wavelength and pulsewidth make different types of lasers valuable for specific purposes. For example, an excimer laser with pulsed UV light of 193 nm has been selected for photorefractive keratectomy (PRK) because it yields an ablation with very little heat release, and because it treats the corneal surface without penetrating the cornea. There are other excimer lasers that use wavelengths from 300-350 nm that will pass through the cornea and into the lens.

High energy light having a wavelength in the range from 100-3000 nm can be produced by various types of laser sources, including those using gases to produce the laser energy, such as the KrF excimer laser; solid state lasers, such as the Nd-YAG and Nd-YLF laser; and tunable dye lasers. No matter the laser source, the physical and chemical effects of coherent light from a laser upon ocular tissue vary according to a number of laser parameters, including wavelength, energy, energy density, focal point size, and frequency. Photodisruption and photoablation describe laser-tissue interactions in which some tissue is destroyed. The term photoablation has been used to describe tissue destruction for photorefractive keratectomy using an excimer laser, as well as for tissue destruction using infrared lasers. Within this application, the term photodisruption is used as described below in the Detailed Description, and may be used herein similarly to uses of the term photoablation in other references.

Of the various sources, infrared nanosecond and picosecond pulsed lasers such as the Nd-YAG and Nd-YLF have been used on the lens because they can focus for treatment deep in a transparent system, and because they remove tissue with minimal effect upon adjacent tissues. The size of the initial tissue destruction using these lasers is relatively large, however. New generation infrared lasers performing in the femtosecond range ($10^{-15}$ seconds) can produce a smaller tissue disruption. (See Lin, U.S. Pat. No. 5,520,679).

SUMMARY OF THE INVENTION

The invention consists of methods for treating the clear, intact crystalline lens of an eye through the creation of microspheres, i.e., small, generally spherical pockets of gas within the lens (i.e., bubbles) for the purpose of correcting presbyopia, other refractive errors such as but not limited to myopia, hyperopia, regular and irregular astigmatism, for the retardation and prevention of cataracts, and treatment of other ocular anomalies. The creation of microspheres in the crystalline lens provides for changes in an ocular lens that may include but are not limited to changes in flexure, mass, and shape. Changes provided by the creation of microspheres generally improve visual acuity of the eye in a manner exemplified by but not limited to the ability to focus more clearly and with a greater range, and to transmit light without scatter and without distortion. The invention recognizes that the intact crystalline lens safely can be treated with a focused, scanning laser, and that treatment of the crystalline lens for correction of ametropias (including presbyopia) may be a superior methodology to refractive surgery on other structures of the eye, including the cornea or sclera, or the implantation of a flexible intraocular (crystalline) lens implant or gel. To enhance safety, the present invention may include concomitant use of antioxidative therapy to minimize any possible side-effects of acute laser radiation exposure during treatment.

In a preferred embodiment, the creation of microspheres occurs through a mechanism that may be referred to as photodisruption. The photodisruption mechanism used to create microspheres, which is described in detail in the following section, produces the beneficial visual effects mentioned above (correction of presbyopia and other refractive errors, retardation and prevention of cataracts, and treatment of other ocular anomalies) via two primary modes of action that are termed (1) photophacomodulation and (2) photophacoreduction. Photophacomodulation refers to any mechanism of light-induced change in crystalline lens tissue that affects its chemical and physical properties and thereby alters the dynamic properties of the crystalline lens including its ability to change shape. Photophacoreduction refers to any mechanism of light-induced change in the crystalline lens whereby the change primarily effects a reduction in the mass or volume of crystalline lens tissue. While these two terms are intended to be used consistently throughout this patent, they may be referred to elsewhere respectively using the terms crystalline lens modulation and volumetric reduction, or in combination using the umbrella term photorefractive lensectomy. By either mode of action, the beneficial effects of the invention are principally achieved through generation of microspheres (as noted above).

Embodiments of the invention that utilize the photophacomodulation mode (effecting a change in the dynamic properties of the crystalline lens) generally generate individual microspheres essentially independent from one another, or may generate individual microspheres that interact, for example by coalescence after generation. Generally, the methods of the invention use the photophacomodulation mode to change lens tissue within the older areas of the ocular lens such as the nucleus, and particularly within specific regions of the juvenile and adult nucleus, since older, more compact tissues are thought to be most responsible for loss in accommodation. In this respect, the present invention can be contrasted with disclosures of the Schachar patents previously cited, in which Schachar proposes treatment of the epithelium, an outer cortex layer, to impair the growth of the epithelium.

Embodiments of the invention that utilize the photophacoreduction mode (effecting volume reduction in the crystalline lens) generally generate microspheres that overlap on formation because their respective sites of photodisruption are contiguous as described below. Generally, the methods of the invention use the photophacoreduction mode to reduce lens tissue volume within the younger cortical areas of the ocular lens, often for the purpose of changing the topography of the exterior surface of the lens. The photophacoreduction mode, however, may be used within the nuclear regions as well.

In a preferred embodiment the methods of the invention such as photophacomodulation or photophacoreduction can be performed as outpatient ophthalmic procedure without the use of general anesthesia and without outside exposure of incised tissue with possible consequent infection.

A further benefit of the present invention for presbyopic correction is that it may actually restore natural accommodation (i.e., the ability of the lens to change its focusing dynamics), instead of attempting to correct for presbyopia through the use of aspherical optics on external lenses, implanted lenses, or the cornea, or requiring the gaze of the eyes to be translated to two or more locations as when using bifocal, trifocal, or progressive lenses.

In another embodiment, treatment according to this invention makes possible the retardation of cataract development. As mentioned above, Koretz observed in 1994 that an inverse relationship exists between lens accommodation and light scatter development, and that the processes leading to light scatter accelerate with decreasing accommodation. In view of the corollary that maintaining or increasing accommodation limits the increase of or reduces light scatter, by surgically increasing accommodation, as mentioned above, embodiments of the present invention may reduce current and anticipated future increases in light scatter. It is hypothesized that such a reduced rate for the processes leading to light scatter is achieved, at least in part, through increased aqueous circulation within the crystalline lens, which results from increased accommodation. As well, the present invention encompasses the creation of microchannels through the photodisruption process that would enhance aqueous circulation within the lens and thereby lead to reduced light scatter. This cataract retardation effect is differentiated from cataract removal (partial or full) and cataract prevention. Cataract retardation has been suggested elsewhere through the use of pharmaceuticals such as antioxidants used over long periods of time that allow for maintaining the transparency of the lens. In this invention, we disclose the use of antioxidants, but only for treatment of the acute or immediate effects of the laser therapy during and after lens irradiation. It is the longer term effects of laser therapy that may lead to a reduction in cataract development through use of certain embodiments of this invention. Whereas cataract removal traditionally has meant the total removal of the lens except for the posterior capsule, and Gwon (U.S. Pat. No. 6,322,556) has proposed removing partial cataracts, both complete and partial removal are different from cataract retardation, which is a benefit of embodiments of this invention.

Further objects and advantages of the invention will become apparent from a consideration of the drawings and ensuing description.

BRIEF DESCRIPTION OF THE DRAWINGS

FIG. 5 illustrates examples of the results of treatment by the individual microsphere formation methodology.

DETAILED DESCRIPTION OF PREFERRED EMBODIMENTS

Figure 3:
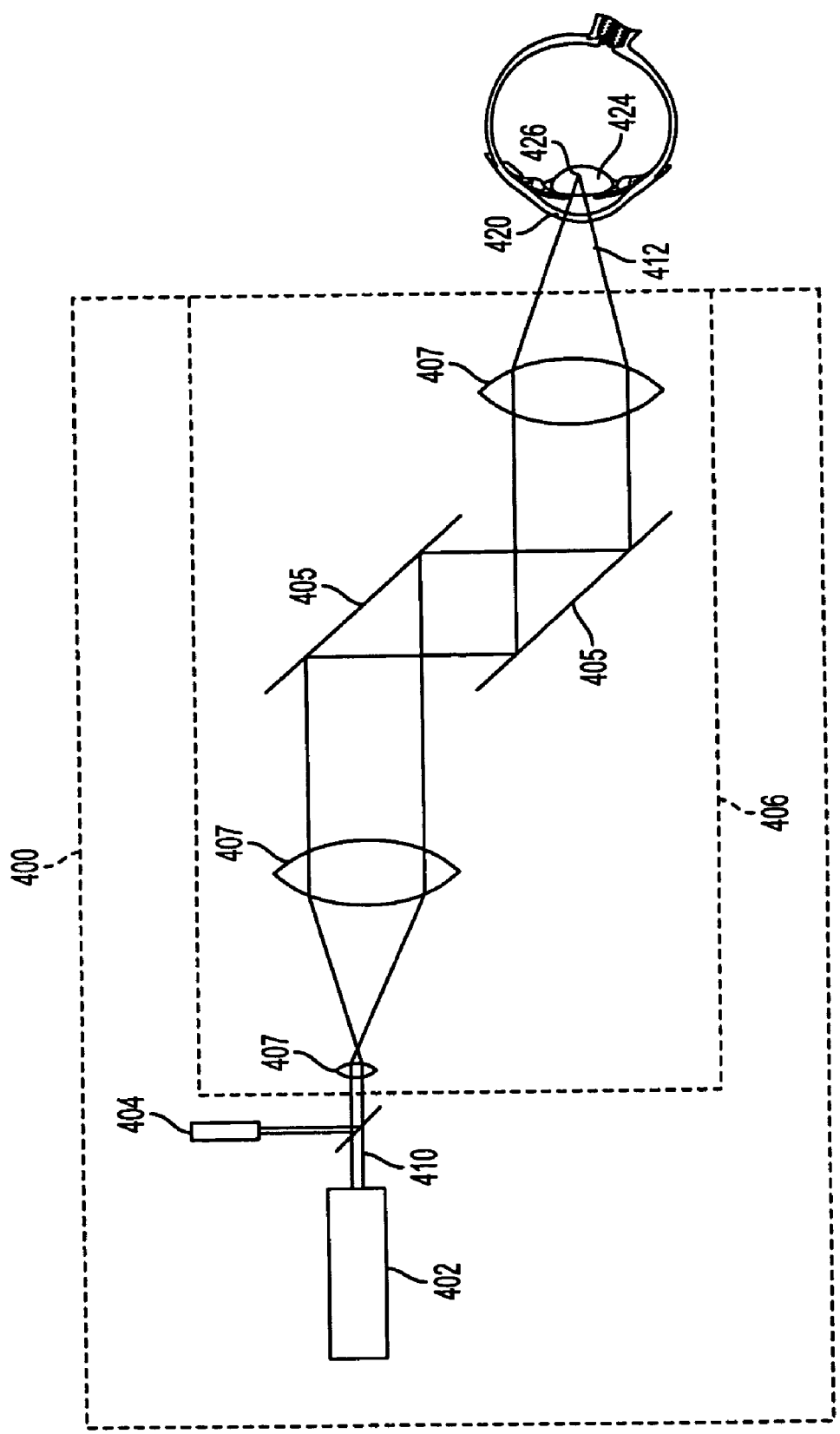
FIG. 3 shows a general schematic of the instrumentation used in embodiments of the present invention.

FIG. 3 provides a basic illustration of the instrument (400) used to perform lenticular refractive surgery (LRS). A laser (402) produces a collimated beam (410) of light having essentially a single wavelength. The laser (402) preferably generates a beam of short duration, high frequency pulses such as discussed in Lin (U.S. Pat. No. 5,520,679), the entire disclosure of which is specifically incorporated herein by reference to the extent not inconsistent with the disclosures of this patent, but may be any laser that provides a beam of sufficient energy and that can be controlled to perform the treatment herein described. The laser beam (410) passes through a beam control system (406), likely comprising mirrors and lenses, for example mirrors (405) and lenses (407), that direct the light in three spatial dimensions and create vergence in the beam. The output from the beam control system (406) is a converging beam (412) that passes through a patient's cornea (420) and is focused on the surface of or within a patient's ocular lens (424) for purposes of treating ametropias and retarding cataractogenesis. The focal point (426) of the converging beam (412) is capable of traversing any point within the three-dimensional space occupied by the ocular lens (424). The surgeon combines knowledge of the patient, the expected ametropias (including presbyopia) to be altered, and lens biometric measurements determined by standard ophthalmic instruments to develop a treatment strategy. Certain of this data is transformed by a computer algorithm that controls the instrument (400) during the treatment, including control of laser parameters such as focal point location, energy level, and pulse duration and frequency. Focal point location during treatment is determined by a scanning program that may be used to reduce unwanted, short-term effects on lens tissue by moving the laser focal point among various areas of the lens, instead of treating immediately adjacent lens areas. A detailed description of an instrument similar to the one shown in FIG. 3, but used for cataract removal, is provided by L'Esperance, Jr. in U.S. Pat. No. 4,538,608, the entire contents of which are specifically incorporated herein to the extent not inconsistent with the disclosures of this patent. Note that in a preferred embodiment the surgeon would receive real-time feedback regarding the precise location of the focal point within the ocular lens and the structural changes as they are occurring. Such data may be obtained by the surgeon through the use of instruments and methods now known to one skilled in the art, or which may be later developed. Advances in eye surgical procedure may easily be incorporated into a procedure that utilizes an embodiment of the present invention.

In an embodiment, the LRS patient is prepared as in cataract surgery or other laser refractive surgical procedure (e.g., PRK). The anterior segment of the eye is prepared by procedures that are common to regular vision testing, including topical anesthetic, dilating drops, and cycloplegia (temporary paralysis of accommodation). Biometric measurements of the lens are taken by A-scan, high frequency ultrasound (B-scan), optical coherency tomography (OCT), or similar instrumental procedures to determine the exact dimensions of the lens, including the geometric center, thickness, and other contour measurements of the nucleus and cortex. Then the eye is held stationary by patient fixation on a coaxial light source. Fixation can be further controlled by a transparent applanation plate fixed to a suction ring on the anesthetized cornea and coupled to the optical pathway of the instrument. The surgeon aligns the instrument and the eye using at least one non-therapeutic helium-neon laser (404), which is focused by the surgeon in the lens at the focal point (426). Once the patient is prepared and the instrument aligned, treatment may begin.

Figure 4:
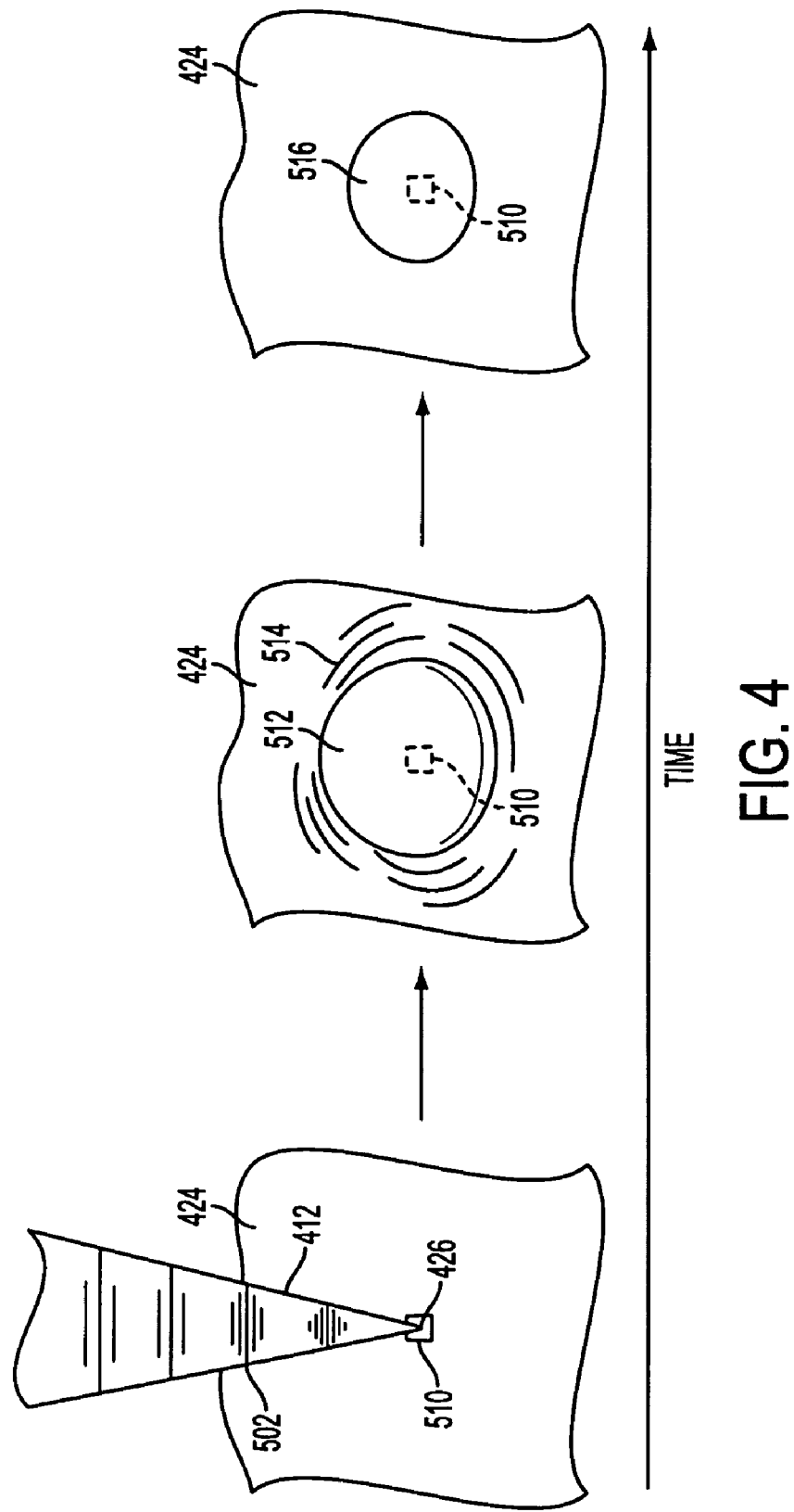
FIG. 4 depicts the mechanism of microsphere formation by photodisruption.

The basis of LRS treatment is the laser induced photodisruption process occurring in the crystalline lens and depicted in FIG. 4. Note that the ocular lens with all of its internal structure (shown in FIG. 2) forms a single unitary structure such that reference to locations "in" or "within" the lens include locations "on" the lens, and the former terms (in and within) will generally be used throughout this patent to include the latter (on).

The photodisruption process is described as follows, beginning with reference to FIG. 3. The convergent laser beam (412) enters the eye through the cornea (420) as light waves, which have been described by L'Esperance (U.S. Pat. No. 4,538,608) as bundles of energy. The laser beam (412) passes through the cornea (420) without damage to that tissue because the energy density (referred to generally as "energy" and also called fluence or fluxure) of the laser within this tissue is at subthreshold levels. That is, only above a threshold energy density not obtained by the laser beam (412) within the cornea (420) will tissue damage occur. See Lin (U.S. Pat. No. 5,520,679) and L'Esperance (U.S. Pat. No. 4,538,608). During LRS treatment, however, the threshold energy level (energy density) is attained or surpassed at the focal point (426) of the converging laser beam (412) within the ocular lens (424). Given that sufficient energy is incident at the focal point (426) the process of photodisruption occurs.

Photodisruption as the term is used herein is a complex, multistep, sequential process, as illustrated in FIG. 4. When a laser pulse (502) traveling the path of the converging beam (412) reaches a first focal point (426) a very small amount of lens tissue (510) is destroyed in a volume essentially centered on that first focal point (426). The volume of lens tissue (510) destroyed depends upon the characteristics of the particular laser pulse (502) (pulse width, wavelength, energy, etc.) incident on the lens (424) and the characteristics of the lens tissue itself. For typical LRS procedures using today's laser technology this volume is likely in a range from about 0.1-500 $\mu m^3$ (e.g., a sphere having a diameter of 0.5-10 $\mu m$). The laser energy incident at the first focal point (426) breaks molecular bonds and ionizes molecules and atoms, converting the tissue (510) at the first focal point (426) from a solid to a plasma (512). At the relatively high energy level of the plasma (512), the matter that has been converted occupies significantly more volume than it did as the solid tissue. Thus, there is a substantial, rapid expansion of the volume occupied by the converted matter, which generates a "hole" in the lens (occupied by the plasma (512)) and creates a shock wave (514) that resonates outwardly from the first focal point (426) into the surrounding tissue. For typical LRS procedures using today's laser technology the shock wave may extend from about 10-500 $\mu m$ from the focal point. Note that the distance the shock wave travels is highly dependent on the pulse width of the laser.

As the procedure continues, the focal point of the laser is moved to a different location in the lens according to the scanning program, and the plasma (512) about the first focal point (426) rapidly converts to a gas (516). The gas (516) fairly rapidly obtains a state of relative equilibrium as compared with the state of the high energy plasma (512). The volume occupied by the gas (516), which is essentially centered on the first focal point (426), is referred to herein as a microsphere. Just as for the volume of tissue (510) destroyed at the focal point (426), the volume of the microsphere (516) depends on all of the laser parameters as well as the tissue characteristics, but for typical LRS procedures using today's laser technology the size of the microsphere will typically be in the range of about 60-15,000 $\mu m^3$ (e.g., a sphere of diameter 5-30 $\mu m$). The volume of the microsphere may be less than the maximum volume occupied by the plasma (512) immediately after expansion due to the altered lenticular system arriving at a state of relative equilibrium after the shock (514) of plasma creation, but could be of greater volume than the plasma (512). The gas in the microsphere, however, is not likely to be in a true equilibrium and eventually likely will be absorbed by the lens tissue causing the microsphere to collapse. Absorption of the gas in the microsphere may occur almost instantaneously, may take up to several days, or may take a longer time. It is possible that in some circumstances the microsphere will not collapse during an extended period of time.

The creation of a microsphere is common to multiple embodiments disclosed herein, yet there are several different methodologies for utilizing the creation of microspheres in performing lenticular refractive surgery (LRS) as is illustrated in FIGS. 5-8. The various methodologies of the invention include (1) individual microsphere formation (FIGS. 5-6), (2) microchannel formation (FIG. 7), and (3) cavity formation or volume reduction (FIG. 8). Each of these methodologies, while distinct, has the potential to both increase the accommodation of the ocular lens and concurrently, consequently, or alternatively, to increase the fluid volume that passes through the various layers of the ocular lens in a given period of time. Such changes likely are the mechanisms whereby embodiments of the present invention effect treatment of ametropias, including presbyopia, and prevention or retardation of light scattering and cataractogenesis.

In an embodiment of the present invention using the individual microsphere formation methodology, the results of which are illustrated in FIGS. 5A-E, numerous individual microspheres (520) are created within the ocular lens (522) in a pattern of predetermined form. The numbers of individual microspheres that are applied to the crystalline lens may vary from a few to hundreds of thousands or more. In the experiments described in the Examples below the number of microspheres applied to a lens has exceeded 300,000. It is generally believed that the application of greater numbers of microspheres is more beneficial. Particularly as technology advances and the microspheres can be made smaller the number of microspheres applied to a lens during a single treatment regimen can be expected to increase further. An anticipated limit to the number of microspheres applied may be provided by the ratio of a minimum microsphere volume that is effective for producing visual improvement in a patient and the volume of the lens being treated.

As an example of this individual microsphere methodology, FIG. 5A depicts a lens (522) treated with microspheres (520) having an aggregate pattern that is an annulus. When using this methodology, individual microspheres (520) may be created at positions within the lens that are separated by sufficient distance so that the microspheres remain predominantly separate, i.e., as a result of the lens tissue characteristics the majority of individual microspheres do not coalesce with an adjacent microsphere. The distance between microspheres necessary to maintain their individual nature will vary, depending on lens and laser characteristics, from about 1 $\mu m$ to about 1 mm, but when using today's technology in the preferred embodiment it will generally be in the range of 10-15 $\mu m$. Additionally, when the placement of microspheres occurs in locations such that a microsphere is anterior to a more posterior microsphere, the more posterior microsphere will be applied first in order to keep the more anterior microsphere from interfering with the creation of the more posterior microsphere.

The useful patterns of microsphere creation in the lens are essentially limited only by the skill of the surgeon operating the instrument. Shown in FIGS. 5A-E are various examples of microsphere patterns in an ocular lens (522). FIGS. 5A-D show a cross section of a crystalline lens laterally oriented as though viewed through a dilated eye and pupil (coronally). FIG. 5E is a cross section of the lens oriented sagittally (ninety degrees rotated from FIGS. 5A-D). FIG. 5A shows an annulus; FIG. 5B shows a disk; FIG. 5C shows radially aligned wedges; FIG. 5D shows radial lines; and FIG. 5E shows the annulus of FIG. 5A or the radial lines of FIG. 5D from a sagittal view. The patterns of microspheres (520) may be applied to the lens essentially throughout the lens volume, except that treatment by LRS generally is intended not to violate the lens capsule (14), which maintains the physiological integrity of the lens and the surrounding aqueous (17) and vitreous (10).

There may be some hesitancy among practitioners to treat the center of the ocular lens along the visual axis, such as by utilizing the disk pattern shown in FIG. 5B. Such hesitancy may arise because of a perceived risk to disrupting lens tissue in the central region of vision (i.e., along the visual axis). Yet, because the microspheres generally collapse in due time, leaving in their absence a volume of lens tissue in the immediate vicinity of the once present microsphere that transmits light without visual disruption, there may be no clinical reason not to apply microspheres within the visual axis.

Figure 6A:
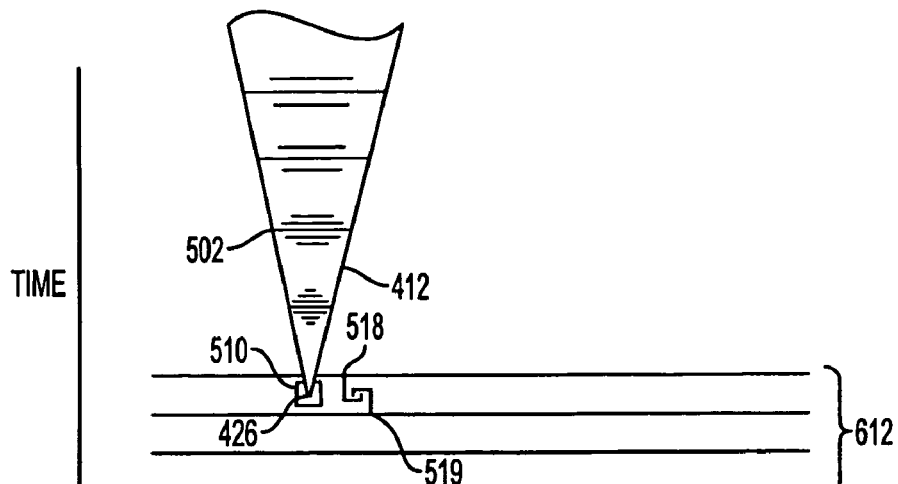
FIG. 6 depicts a mechanism of individual microsphere interaction producing a beneficial separation of lens fibrils.
Figure 6B:
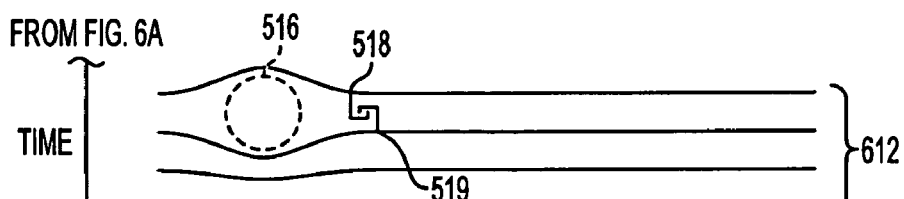
Figure 6C:
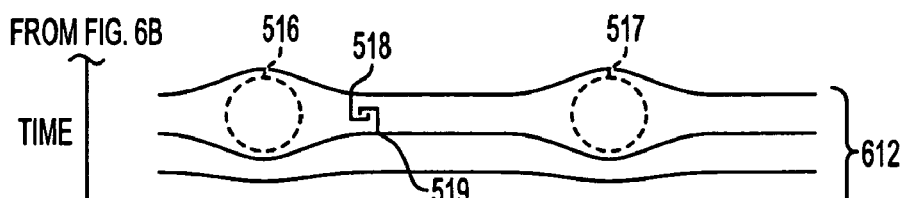
Figure 6D:
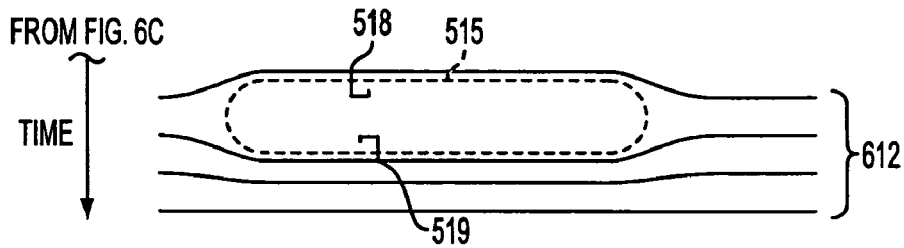

In an alternate embodiment individual microspheres are created at such distances from one another that at least some microspheres do coalesce. An illustration of how an individual microsphere may act in concert with another microsphere through coalescence is provided in FIGS. 6A-D. In FIG. 6 the fibrils (612) of the lens are depicted as straight lines equidistant from one another. Note that the elements of FIG. 6 are not drawn to scale, but are depicted in a manner that enhances the illustration of this written description. As described above, the converging laser beam (412) is focused at the focal point (426) within the lens, and by the process of photodisruption a first microsphere (516) is created, pushing apart or cleaving the fibrils (612) in the vicinity of the first microsphere (516). The energy of creation of the first microsphere is in the first instant contained within the fibrils adjacent to the first focal point and the interstices therebetween as shown if FIG. 6B. However, the forces resulting from microsphere creation, including plasma formation and the consequent shock wave (514) will likely cleave the laminar fibrils of the crystalline lens along the boundary between the fibrils. The cleavage of laminar fibrils of the crystalline lens by a dull surgical tool has been described by Eisner in *Eye Surgery* (1980), which is explicitly incorporated herein by reference to the extent not inconsistent with the disclosures of this patent. As LRS treatment continues, a second microsphere (517) is created, cleaving fibrils in its vicinity. The forces of microsphere creation that cleave fibrils (612) are such as to extend the separation between the fibrils (612) along the distance between the microspheres (516 and 517). The separation may extend along the entire distance between the microspheres (516 and 517) as shown in FIG. 6D. At the point that the separation between fibrils (612) has extended along the entire distance between microspheres (516 and 517), the microspheres will merge into a single expanded microsphere (515), as shown in FIG. 6D.

Also shown in FIG. 6 is a representation of the interconnections (518 and 519) between fibrils (612). These interconnections could be any form of engagement between fibrils, including interdigitations, van der Waals attractions, or disulfide bonds. The separation of fibrils (612) may be such that the interconnections (518 and 519) are disrupted to the extent that they no longer act to connect the fibrils (612), as shown in FIG. 6D. Both the separation of fibrils and the disruption or disengagement of the interconnections (518 and 519) allows a greater range of motion of fibrils (612) with respect to one another, including a greater ability to translate relative to one another. This greater range of motion, in turn, leads to increased flexibility of the crystalline lens as a whole, or at least in the region treated, which results in greater accommodation and, therefore, correction of presbyopia. Thus, the present invention is theorized to effect increased accommodation by decreasing tissue density and disrupting fibril interconnections.

While it is shown in FIG. 6 that disengagement of the fibril interconnections occurs as a result of the interaction or coalescence of microspheres (FIG. 6D), the same disruption or disengagement can and does occur via application of a single miscosphere. As described above the creation of a microsphere will likely cleave the laminar fibrils along the fibril boundary. Because cleavage along fibril boundaries may occur whether or not microspheres coalesce, similar beneficial results (e.g., increased accommodation) may be achieved in either instance.

Figure 1:
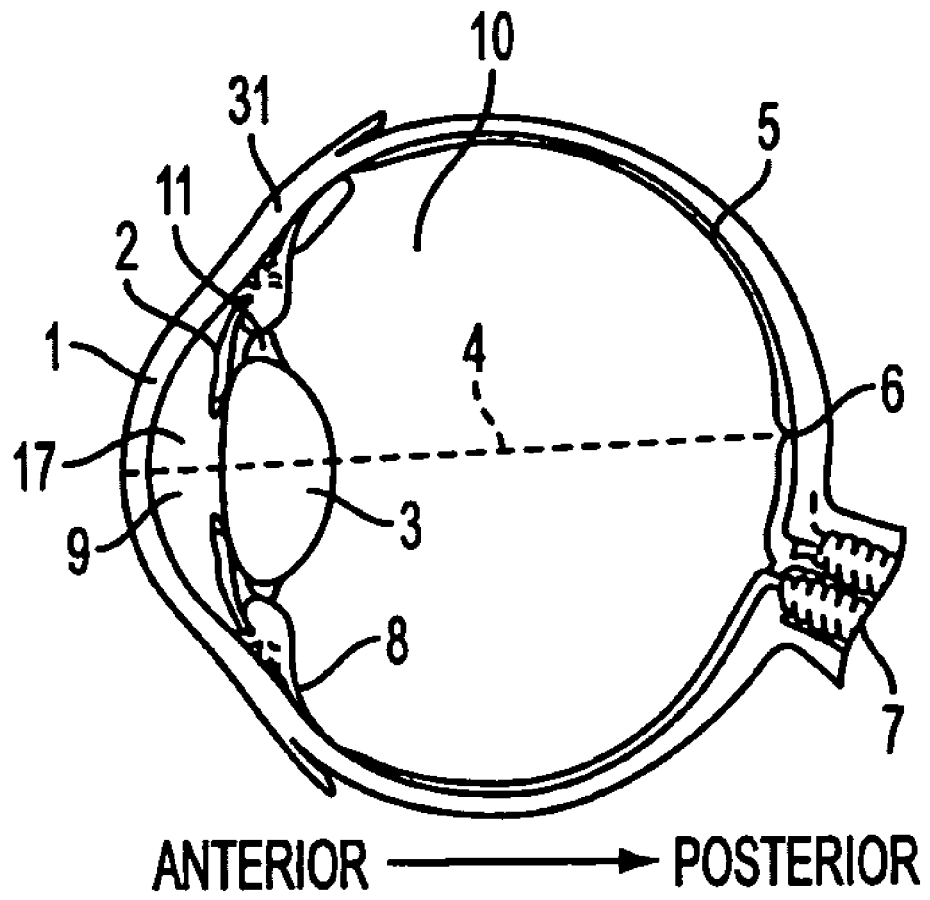
FIG. 1 shows the gross anatomy of the eye.
Figure 2:
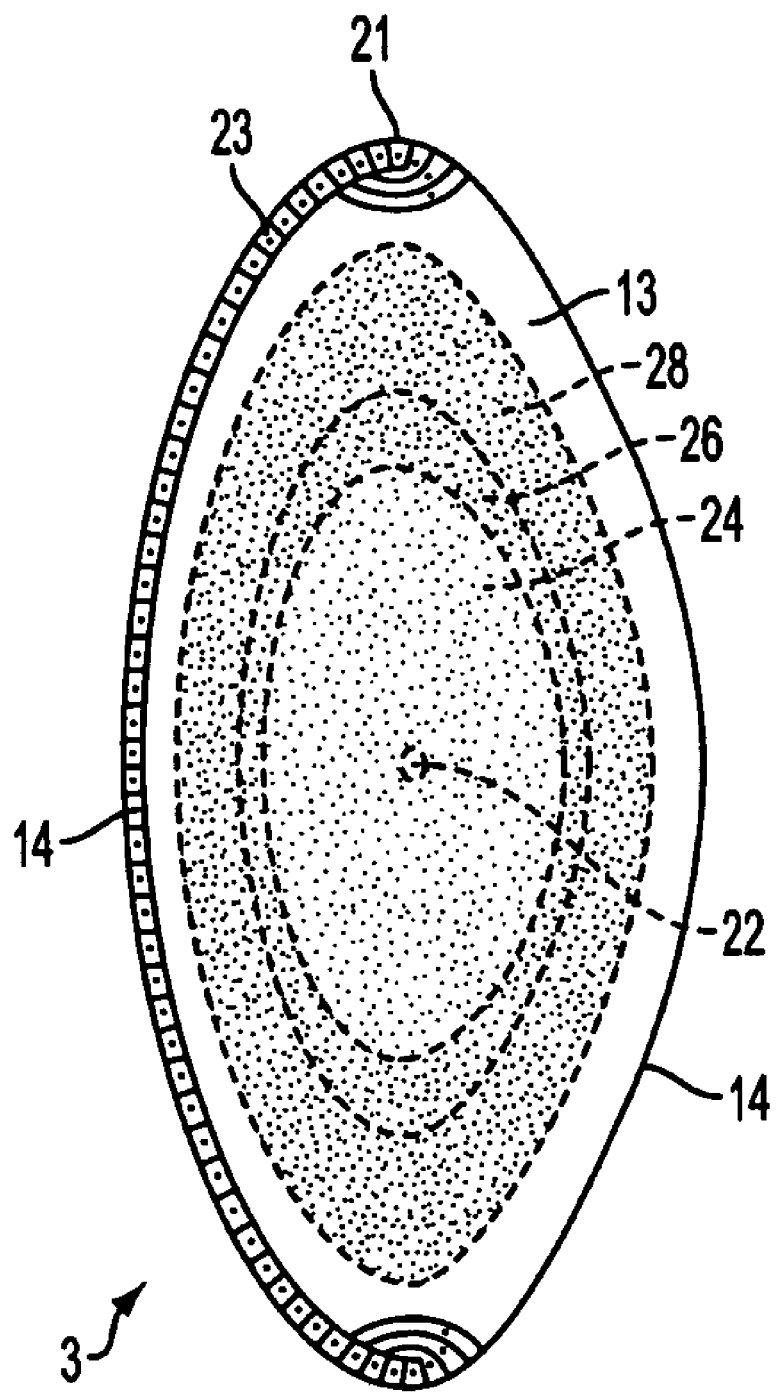
FIG. 2 is an enlarged view of the crystalline lens showing its internal structure.

When using the individual microsphere formation methodology, microspheres are generally applied to areas of the crystalline lens which are the least flexible. In particular the juvenile nucleus (26) and the adult nucleus (28), seen in FIG. 2, are denser tissues within the lens and are considered the least flexible, and therefore are likely areas of treatment. In addition, it may be advantageous to treat other areas of the nucleus, including the infantile nucleus (24) where the older tissue is not so compacted, and even the cortex (13). Treatment of these older, denser, and less flexible areas is likely to have greater benefit than treatment elsewhere in the lens since the fibril structure of the older, denser lens areas is known to contain greater chemical cross-linking, more interfibril engagements, more compaction, and less transparency. Therefore, treatment of these less flexible areas with individual microspheres as described above may well achieve a decoupling of fibrils, i.e., a tearing apart of the macromolecular structures that form in the older lens tissue by breaking cross-linkages, disengaging interfibril engagements and generally separating the compacted layers of the lens tissue (e.g., as shown in FIGS. 6A-D).

The presentation of microspheres to the lens, i.e., the creation of microspheres in the lens as just described, is a technique that induces a softening of lens tissue. In particular, the creation of microspheres in the ocular lens and the consequent disruption of fibril interconnections (518 and 519) can lead to a greater flexibility and an increased range of motion of the fibrils (612), which, in turn, may generate an increase in lens accommodation or allow for the maintenance of the present level of accommodation for a longer period of time, and therein may be a treatment for visual impairments, especially for presbyopia. Using the methodology of individual microsphere formation to treat a presbyopic lens may generate increased accommodation in the range from 0-8 Diopters, which can have the effect of providing a 45 year-old lens with the flexibility of a typical 35 year-old lens. As described above, when discussing Koretz's observations, such an increase in or maintenance of accommodation may also aid in reducing light scatter or reducing the rate at which light scatter is created.

In alternate embodiments of the individual microsphere formation methodology, in addition to or as an alternative to the benefits in relation to reducing presbyopia, increasing accommodative potential may correct some amount of myopia, hyperopia, astigmatism, or aberration. That is, an increase in accommodation may provide the lens the added flexure and biomechanical changes needed to correctly focus an image in response to neural feedback, thereby correcting myopia, hyperopia, astigmatism, or aberration.

In a further embodiment using the individual microsphere formation methodology, it is also possible to achieve targeted flexural changes in the ocular lens, that is, flexural changes at specific locations or within certain regions, so as to generate useful biomechanical differentials across the lens volume. These biomechanical differentials may include differential flexibilility or thickness between regions. Purposely creating a lens wherein certain regions are more flexible or thicker than others may allow for improved focusing capability. For example, for the correction of hyperopia, achieving more flexure along the visual axis (4), as opposed to the periphery of the lens, would allow a greater range in lens shape through the center of the lens so that when tension on the crystalline lens was relaxed, the lens would be more convex than before treatment, correcting the hyperopia to at least some extent. Similarly, myopia might be corrected by the application of individual microspheres to achieve targeted biomechanical changes in the ocular lens at the periphery, the visual axis, or at some other location, so as to allow for a less convex lens shape when the crystalline lens is under full constriction as it would be when viewing a distant object. The creation of biomechanical differentials in flexibility and thickness are particularly important with respect to the treatment of astigmatism because the focusing potential of the lens must be the same in the all focal planes.

Figure 7:
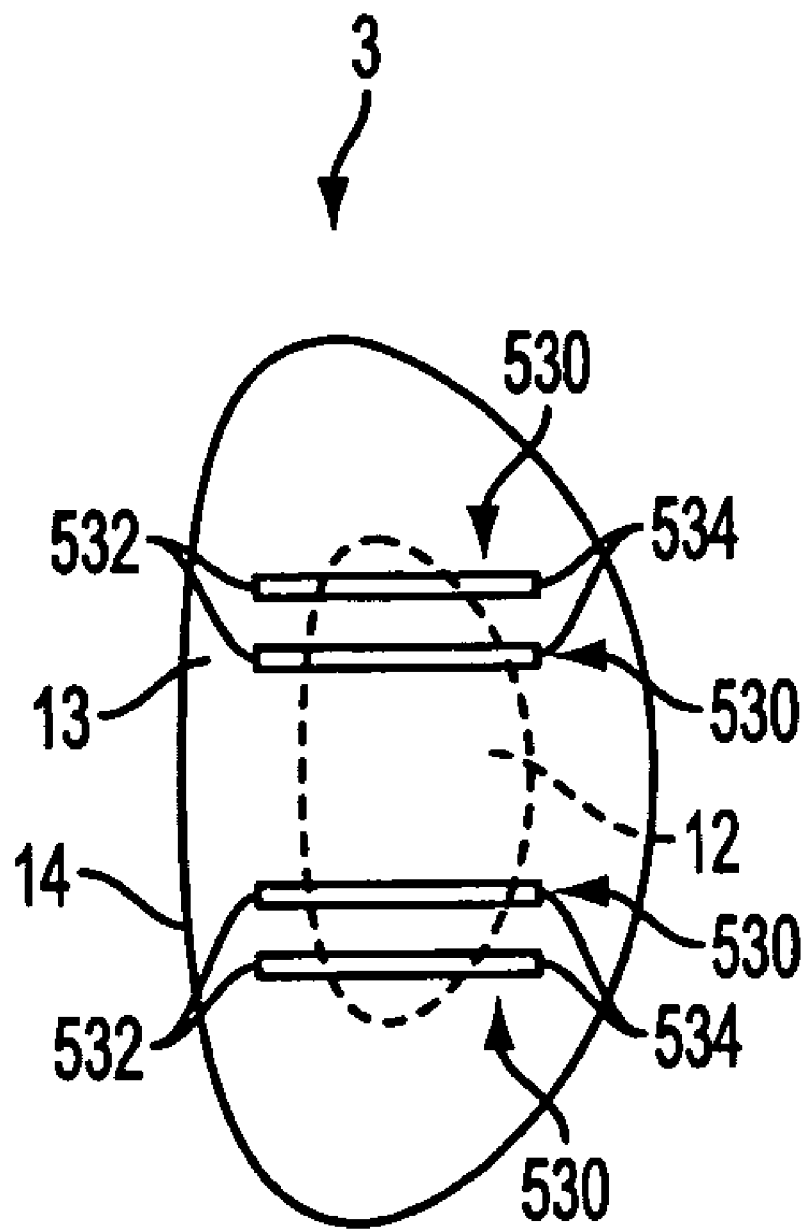
FIG. 7 depicts microchannels created in a lens.

In another embodiment of the present invention, the results of which are illustrated in FIG. 7, microspheres are created within the ocular lens (3) in close proximity to one another in a generally sequential pattern from posterior to anterior positions in the lens. In this embodiment the microspheres are created at positions within the lens that are separated by an insufficient distance to maintain the individuality of the microspheres. Not only are the individual microspheres created close enough to one another that they do coalesce, but also according to this embodiment the small volumes of tissue removed (e.g., volume 510 in FIG. 4) are contiguous. By moving the laser focal point generally in an anterior direction from the starting point (534), and removing contiguous volumes of tissue (e.g., volume 510 in FIG. 4), an open channel (530) in the lens tissue can be created. This open channel (530) is referred to as a microchannel (530) and is different from the embodiment described above and illustrated in FIG. 6 in which the microspheres are placed close enough to coalesce but in which the small volumes of tissue removed are not contiguous. An additional difference from the embodiment illustrated in FIG. 6 is that a microchannel of this embodiment traverses a path generally perpendicular to the length of the fibers. Even though some of the gas created in the microchannel during the photodisruption process may be absorbed by the remaining lens tissue, sufficient lens tissue mass has been removed along the path of the microchannel that even with some reduction in channel volume due to gas absorption, the channel remains generally open. Also different from the embodiment of FIG. 6, the microchannels of this embodiment are created in such dimension—i.e., sufficient tissue volume is removed—that they remain as open channels long after the surgery, possibly on the order of years or longer.

The microchannel (530) is generally characterized by a path length from the starting point (534) to the endpoint (532) that is greater in distance than any channel dimension perpendicular thereto. That is, if the microchannel is created having a generally circular cross section, its length is greater than the cross section diameter. The starting and ending points (534 and 532) for the microchannels may be the sutures which are known to be a part of the fluid flow system of the lens. While the length of a microchannel is generally along a path essentially parallel to the visual axis, the microchannel may follow a non-linear path along a length in the general direction from posterior to anterior. As well, although the circular cross section is the preferred shape, any feasible cross sectional shape may be used.

The microchannels aid in fluid transport through the structures of the ocular lens, thereby allowing an exchange of antioxidants, nutrients, and metabolic by-products between the aqueous and portions of the lens to which there was previously insufficient fluid flow. As described in the Background section the older tissues in the lens, primarily in the nucleus (12), are generally more dense and show a build-up of cellular by-products. The increased fluid transport in these older tissues such as is allowed by the microchannels may retard or reverse the processes that lead to declining accommodation (i.e., presbyopia) and light scattering. The microchannels may be used alone as a treatment strategy or may be used to supplement the enhanced fluid flow generated by increasing the flexure of the lens for the correction of presbyopia.

In another embodiment, illustrated in FIG. 8, mass and volume reduction of the lens tissue generally at the periphery is accomplished through the creation of microspheres in such proximity that the small volumes of tissue removed (e.g., volume 510 in FIG. 4) in the photodisruption process are contiguous. This methodology is generally referred to as photophacoreduction. While the methodology is essentially the same as in the previous embodiment in which microchannels are created through tissue removal, the location, geometry, and purpose of the volume removal of this embodiment is substantially different.

Figure 8A:
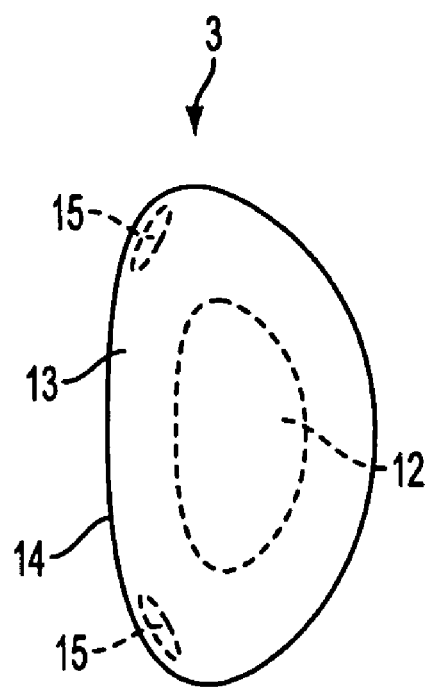
FIG. 8 depicts the results of cavity formation or volume reduction within the lens, resulting in a new lens surface topography.
Figure 8B:
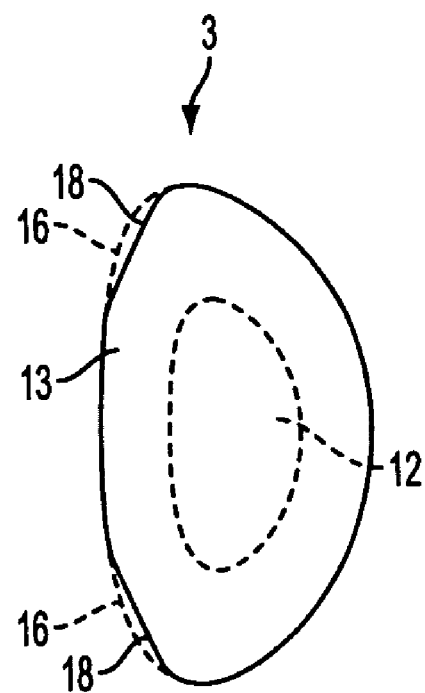

In this embodiment the removal of contiguous volumes by photodisruption creates a cavity (15) in the cortex (13) as opposed to the nucleus (12) of the ocular lens (3). FIG. 8A shows the location of the cavity (15) in the lens (3) where the lens (3) is still in the shape it had prior to cavity (15) formation. The cavities (15) can follow the contour of a fibril layer of the lens to reduce the numbers of fibers that are interrupted, or may be created to maximize the number of fibers interrupted. The result of the procedure of this embodiment is a collapse of the capsule (14) in the region of the tissue removal wherein the path of the capsule (16) prior to the collapse is longer and located generally anterior to the path of the capsule (18) after collapse. FIG. 8B shows the lens shape after collapse of the cavity (15), at which time, as a result of the collapse, the cavity (15) is no longer present in the lens as remaining lens tissue has collapsed into the cavity (15). Due to cavity (15) formation the lenticular capsule (14) may also loosen causing a reduction in the useful energy imparted to the lens by the zonules. If necessary the capsule can be tightened by thermoplasty using infrared radiation without opening a hole in the capsule. Using thermoplasty reduces the length of the lens capsule (14) in the region about the volume reduction. Collapse of the lens (3) may occur naturally as a result of volume removal, or may be induced as a result of capsule thermoplasty. Treatment by photophacoreduction may best be accomplished in the less dense tissues of the cortex (13) or the infantile nucleus (24), but otherwise may be performed in essentially any lens location.

Generally, in the embodiment shown in FIG. 8, the procedure will be performed for the purpose of altering the exterior topography of the ocular lens as a method for correcting ametropias other than presbyopia. The beneficial effect of this embodiment may be a change in the refractive power of the lens at the location at which a topography change occurs so as to lessen or remove completely the myopic, hyperopic or astigmatic condition of a person's vision. Cavities toward the optical center cause a surface collapse that produce a less convex anterior or posterior surface, and that reduce myopia. Alternatively, placing the cavity toward the equator may reduce hyperopia. Creating a cavity of varying thickness induces lenticular astigmatism which may counteract an existing astigmatism. While a change in refractive power is a possible benefit, the lens capsule collapse may also cause a different angular insertion to the zonules and may thereby provide a more efficient ciliary muscle action allowing for some correction of myopia, hyperopia, and presbyopia. An additional benefit to the removal of lens mass and volume near the periphery, however, may be an increase in accommodation.

A further alternative embodiment is the prevention of cataract formation through any of the methodologies described above: 1) individual microsphere formation, 2) microchannel formation, and 3) volume removal. While there is a connection between presbyopia and the development of light scatter and lens opacification, success in cataract retardation may be independent of the success of treatment for presbyopia.

In an alternative embodiment, the application of numerous individual microspheres may produce a combined net increase upon the lens thickness that will also result in an increase in accommodation. The additional volume that results from microsphere formation may vary as the lens is pulled upon by the ciliary muscle and alternately relaxed. Due to the effects of tension on the lens, the additional volume from microsphere formation may be greatest when the lens is relaxed. The result of this kind of relaxed volume change depending on the tension in the lens is actually an increase in accommodation.

A still further alternate embodiment is the concomitant use of drugs to reduce inflammation and the effects of free radicals and debris within the lens portions of the eye before, during, and after the procedure. Antioxidative drugs, such as galactose, glutathione, and penicillamine, can react locally with any active by-products and facilitate the reduction of free radicals generated during the surgery. These drugs enter the circulatory, lymphatic, and intraocular systems after oral or topical administration, then naturally penetrate the lens matrix from the aqueous. After treatment according to an embodiment of this invention, their transport may be aided by the newly gained flexure as well as newly created microchannels. Also, anesthetics, mydriatics and cycloplegics are used at the time of the treatment as in other intraocular surgeries. Miotics for pressure control, corticosteroids and/or non-steroidal anti-inflammatory drugs (NSAIDS) also may be used after surgery.

Each of the methodologies just described can be carried out using lasers for which the emitted light has a variety of physical parameters. The light used may be in wavelengths from ultraviolet through visible and into the infrared regions of the electromagnetic spectrum, any of which wavelengths may be useful in carrying out embodiments of this invention. A range of wavelengths from about 100 nm to about 2000 nm may be useful in embodiments of this invention. Because of the general transparency of the tissues of the anterior portions of the eye to visible light (allowing visible light to pass through the eye and to be focused on the retina), the preferred wavelength ranges do not include the visible wavelengths but are in the ultraviolet region from about 310-350 nm and in the infrared region from about 700-1500 nm. There are advantages and disadvantages to each of these ranges as mentioned previously. The most preferred wavelengths, and those which have been most extensively tested for use in embodiments of this invention are the infrared wavelengths from about 800-1300 nm, and particularly from about 800-1000 nm.

Preferred ranges for other laser parameters include the following. The preferred pulse width is in the range from about 1 fs to about 500 ps, with the more preferred range being from about 50 fs to about 500 fs. The preferred pulse energy has the range of about 0.1 mJ to about 10 mJ per pulse with the more preferred range being from about 0.5 to about 50 mJ per pulse. The preferred frequency for pulse delivery has the range of about 1 Hz to about 50,000 Hz, with a more preferred range of about 1,000 Hz to about 20,000 Hz. The pulse energy would be within the range of about 0.25 mJ/pulse to about 1 J/pulse, the more preferred range being from about 0.5 mJ/pulse to about 50 mJ/pulse.

Steps included in embodiments of the present invention to maximize the safety and efficacy to the lens and other vital parts of the eye during treatment include maintaining the lens capsule intact, i.e., keep from physically destroying the lens capsule, which would otherwise thereby allow the lens contents to have an opening to the aqueous, which is well known to cause cataract. Another safety procedure is to control the cone angle of the laser beam such that extraneous light not absorbed by interactions at the focal point is masked by inert posterior matter from damaging other tissue. Preferred cone angles range from about 2 degrees to about 40 degrees, with the more preferred cone angles being from about 5 degrees to about 15 degrees. Further, control of light energy parameters (e.g., wavelength, pulse frequency, etc.) and the use of pharmacological agents may be used to minimize pathological changes to the cornea, equatorial (germinal) lens epithelium and fibril, ciliary body, and the perimacular region of the retina.

While a fairly specific mechanism has been described for the process of photodisruption, other mechanisms are encompassed by this invention. Any mechanism through which a microsphere as described herein can be created may work to produce the beneficial results described herein. The various mechanisms by which a microsphere may be created in the crystalline lens include those that result from the application of a wide variety of energy sources. Discussed in detail herein is the use of laser light (particularly in the infrared and ultraviolet wavelengths) as an energy source for creation of a microsphere, but any energy source and delivery method that can be used to create a microsphere in the crystalline lens may be suitable for use in this invention. Alternate sources of energy include but are not limited to mechanical sources such as a water jet or scalpel, sound or ultrasound energy, and heat.

In an alternate embodiment, any of the above described methodologies can be performed with the use of a probe inserted through a corneal incision for the purpose of delivering the energy necessary to create the microspheres. Use of a probe to deliver energy would allow light energy and various other methods of transferring mechanical energy, such as by water jet, to be utilized in embodiments of this invention. In this alternate embodiment the probe for delivery of energy may abut the lenticular surface or may be held at some distance therefrom. This alternative embodiment is preferred for the delivery of sources of energy that are not efficiently transported through the anterior portions of the eye.

Presently, the preferred group of patients on which to carry out this treatment is emmotropic low hyperopic subjects with spectacle prescriptions of less than 3.00 D. Preferred patients are pre-presbyopic, in their early 40's, with 3-5 Diopters of accommodation, and have undergone a full-dilated eye exam to determine the following: a) no prior history of eye disease, trauma, cataracts, or collagen vascular disease; b) normal gonioscopic findings; and c) no significant systemic diseases.

The properties of the crystalline lens and lasers identified herein allow for treating the clear, intact, crystalline lens for the purpose of correcting presbyopia, refractive errors, higher order aberrations, and other disease conditions including cataract prevention and retardation. A multiplicity of methodologies makes it possible to address the various probable causes of presbyopia. The result of treatment for presbyopia according to an embodiment of this invention is likely to restore from five to eight diopters of accommodation and to postpone presbyopic development for 5-8 years or more. The same processes of lenticular hardening and enlargement will continue after treatment and will eventually cause a reduction in accommodation, resulting in delayed presbyopia onset after treatment. An additional treatment may prove safe and efficacious, which would further delay presbyopia. In at least one embodiment, all of the changes to the crystalline lens are made under the control of a computerized laser, which can make specific modifications either separately or together for the treatment of presbyopia, myopia, hyperopia, and astigmatism, as well as for cataract prevention and retardation.

EXAMPLES

Cadaver Lens Study

As a first step, a precision technique was verified on 36 human cadaver lenses, where the age-dependent, flexural characteristics of the lenses were compared with results in studies of other designs. In the second step, an Nd-YAG laser was used to produce a 2-4 mm annulus in one of a pair of lenses from 11 donors while the fellow lens was kept as the control. The Nd-YAG pulse produced microspheres in the range of 50-500 µm diameter. An annular laser pulse pattern of 100 suprathreshold pulses were placed in the center of the treated lens, to produce a doughnut shaped pattern of microspheres. A simulated accommodation was created using a rotating base upon which the lens revolved at up to 1000 rpm. Rotational deformation was measured by changes in the central thickness and in anterior lens curvature as measured by two different techniques. When comparing the matched lenses, lens flexibility differences were demonstrated by statistically significant differences in lens curvature and thickness. That is, rotational deformation flattened the curvature and decreased the thickness of the treated lens, compared to the untreated, less flexible lens. Dioptric changes were calculated at as much as 8 diopters of change. The greater lens formation among laser treated lenses compared to their fellow untreated control lenses showed that the first demonstrated example of increasing flexure and accommodation by laser treatment of the crystalline lens, and therefore photophakomodulation may be a possible lens treatment for presbyopia.

Saftey Study

Six rabbits were treated in one eye with a femtosecond laser generating approximately 300,000 microspheres in either of two patterns, an annulus or radial lines, and at various degrees of microsphere separation. The study was set up to observe cataractogenic potential of microspheres in live animals three months after laser treatment. The animals were sacrificed at three months and their lenses were examined for early and advanced cataract formation through gross viewing, light and electron microsopy. Furthermore, optical quality tests using known scanning laser light scattering techniques over the full cross section of the lens demonstrated no increase in light scatter or refractive distortion in treated lenses relative to their match controls. The results and implications of this study to the invention were as follows.

a) Ultrashort low energy pulses can be efficiently delivered transcorneally into the lens nucleus and cortex of living subjects.

b) Femtosecond laser pulses of low energy produce very limited lens tissue disruption with a myriad of small microspheres. Initially, a ground glass appearance over the treated area is seen, was not present grossly or under magnification after three months.

c) No optical distortion was seen using exacting, diffractional techniques three months after the lens was treated and compared with its control lens.

d) No cataractous changes were seen grossly in the lenses, except in one instance where both the treated and untreated excised lenses developed cataracts.

e) Electron microsopy showed limited disruption of lens tissue adjacent to the treated area. There is small electron dense film at the juncture of the microsphere and other tissue.

While the present invention has been disclosed in connection with certain preferred embodiments, this description should not be taken as limiting the invention to all of the provided details. Modifications and variations of the described embodiments may be made without departing from the scope and spirit of the invention. Various and multiple alternate embodiments are encompassed in the present invention disclosure as would be understood by one of ordinary skill in the art.

The invention claimed is:

1. A method for increasing the flexibility of the ocular lens of the eye, comprising the steps of:
 a) selecting a location within the ocular lens of an eye;
 b) creating a microsphere at the selected location, wherein said microsphere comprises a gas-filled bubble of generally spherical shape; and
 c) repeating the steps of selecting and creating at a plurality of locations within the ocular lens so as to increase the flexibility of the lens
 wherein the microspheres created in step c) remain predominantly separate until after the last microsphere has been created.

2. The method of claim 1 wherein said increase in flexibility increases accommodation of the lens.

3. The method as set forth in claim 1 wherein the increase in flexibility creates no significant change in the anterior to posterior thickness of the lens.

4. The method of claim 1 wherein said microspheres are created with a separation in the range of about 2 µm to about 20 µm.

5. The method as set forth in claim 1 further including the step of: allowing said microspheres to collapse while maintaining said increase in flexibility.

6. The method as set forth in claim 5 wherein said collapse decreases the anterior to posterior thickness of the lens.

7. The method of claim 1 wherein said increase in flexibility corrects an optical anomaly of the eye.

8. The method of claim 7 wherein said optical anomaly comprises a refractive error.

9. The method of claim 8 wherein said refractive error is myopia, hyperopia, presbyopia, regular astigmatism, irregular astigmatism, or aberrations.

10. The method for increasing flexibility as set forth in claim 9, wherein the step of repeating generates at least one change in the ocular lens resulting in at least one effect selected from the group consisting of: alteration of lens surface curvature, increased lens flexibility, increased accommodation, reduced light scatter, reduced rate of increase in light scatter, and reduced rate of loss of accommodation.

* * * * *

UNITED STATES PATENT AND TRADEMARK OFFICE
CERTIFICATE OF CORRECTION

| | |
|---|---|
| PATENT NO. | : 7,655,002 B2 |
| APPLICATION NO. | : 10/750789 |
| DATED | : February 2, 2010 |
| INVENTOR(S) | : Myers |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1244 days.

Signed and Sealed this
Eighth Day of February, 2011

David J. Kappos
*Director of the United States Patent and Trademark Office*